(12) United States Patent
Seba et al.

(10) Patent No.: US 11,284,808 B2
(45) Date of Patent: Mar. 29, 2022

(54) DEVICE AND METHOD FOR MEASUREMENT OF VITAL FUNCTIONS, INCLUDING INTRACRANIAL PRESSURE, AND SYSTEM AND METHOD FOR COLLECTING DATA

(71) Applicant: Linet spol. S.R.O., Slany (CZ)

(72) Inventors: Petr Seba, Bartosovice v Orlickych horach (CZ); Filip Studnicka, Hradec Kralove (CZ); Vladimir Kolar, Slany (CZ)

(73) Assignee: Linet spol. S.R.O., Slany (CZ)

(*) Notice: Subject to any disclaimer, the term of this patent is extended or adjusted under 35 U.S.C. 154(b) by 129 days.

(21) Appl. No.: 16/776,620

(22) Filed: Jan. 30, 2020

(65) Prior Publication Data

US 2020/0163564 A1 May 28, 2020

Related U.S. Application Data

(63) Continuation-in-part of application No. 16/304,160, filed as application No. PCT/CN2017/000042 on Jun.
(Continued)

(30) Foreign Application Priority Data

Oct. 11, 2014 (CZ) .............................. CZ2014-696
Jun. 22, 2016 (CZ) ............................... CZ2016-366

(51) Int. Cl.
*A61B 5/03* (2006.01)
*A61B 5/0205* (2006.01)
(Continued)

(52) U.S. Cl.
CPC ............ *A61B 5/031* (2013.01); *A61B 5/0205* (2013.01); *A61B 5/14503* (2013.01); *A61B 5/6814* (2013.01); *A61B 2562/0214* (2013.01)

(58) Field of Classification Search
CPC .......... A61B 2562/0214; A61B 5/0205; A61B 5/02141; A61B 5/031; A61B 5/1102; A61B 5/14503; A61B 5/6814; A61B 5/6892
See application file for complete search history.

(56) References Cited

U.S. PATENT DOCUMENTS 4,884,578 A * 12/1989 Morgenstern ........ A61B 5/1102
600/483
4,984,567 A 1/1991 Kageyama et al.
(Continued)

FOREIGN PATENT DOCUMENTS

DE 3130326 A1 2/1983
EP 1 837 638 A1 9/2007
(Continued)

OTHER PUBLICATIONS

LINET Group SE, "LINET introduces groundbreaking method for monitoring intracranial pressure," Oct. 13, 2014, pp. 1-3, XP55239403, http://www.linet.com/-/media/Files/Website/linel/riews/20141013 Press_ Release_ Groundbreaking_ method .ashx (retrieved on Jan. 7, 2016).
(Continued)

*Primary Examiner* — Jonathan T Kuo
(74) *Attorney, Agent, or Firm* — Thedford I. Hitaffer; Hitaffer & Hitaffer, PLLC

(57) ABSTRACT

A device for non-invasive monitoring of intracranial pressure (ICP) may include a sensor, a processor unit, a device for recording electrical activity of the heart, and a device for invasive measurement of arterial blood pressure. The sensor monitors mechanical movements caused by bloodstream dynamics. A mathematical model and a relation between the start of a R-wave and a time delay of a mechanical movement of a patient's head are used to determine the ICP. A device for monitoring patient's vital functions may also
(Continued)

measure respiratory and heart rate. The sensor may employ a piezoelectric transducer, which may form a measuring electrode of a measuring capacitor. In addition, a comparator capacitor may be used to increase resistance in changes in measuring conditions. Data from a plurality of measuring devices may be collected and processed in a cascading manner.

35 Claims, 11 Drawing Sheets

Related U.S. Application Data 22, 2017, now Pat. No. 11,076,789, and a continuation-in-part of application No. 16/304,157, filed as application No. PCT/CN2017/000041 on Jun. 22, 2017, now abandoned, and a continuation-in-part of application No. 15/518,402, filed as application No. PCT/CN2015/000113 on Oct. 1, 2015, now abandoned.

(51) Int. Cl.
 *A61B 5/00* (2006.01)
 *A61B 5/145* (2006.01)

(56) References Cited

U.S. PATENT DOCUMENTS

| | | | |
|---|---|---|---|
| 5,448,996 A | 9/1995 | Bellin et al. | |
| 5,617,873 A * | 4/1997 | Yost | A61B 8/0808 33/511 |
| 5,999,848 A | 12/1999 | Gord et al. | |
| 6,491,647 B1 | 12/2002 | Bridger et al. | |
| 6,984,207 B1 | 1/2006 | Sullivan et al. | |
| 7,652,581 B2 | 1/2010 | Gentry et al. | |
| 7,699,784 B2 | 4/2010 | Wan Fong | |
| 8,211,031 B2 * | 7/2012 | Poupko | A61B 5/031 600/506 |
| 8,536,988 B2 | 9/2013 | Ritter | |
| 8,538,625 B1 | 9/2013 | Lowchareonkul | |
| 9,131,896 B2 * | 9/2015 | Burger | G01L 27/002 |
| 9,826,934 B2 * | 11/2017 | Oliveira | A61B 5/6803 |
| 10,376,216 B2 | 8/2019 | Kolar et al. | |
| 2003/0115966 A1 | 6/2003 | Naoohiro | |
| 2004/0087863 A1 | 5/2004 | Eide | |
| 2005/0015009 A1 | 1/2005 | Mourad et al. | |
| 2006/0079773 A1 * | 4/2006 | Mourad | A61B 8/00 600/438 |
| 2006/0131855 A1 | 6/2006 | Kreuzer | |
| 2007/0021680 A1 | 1/2007 | Mills | |
| 2007/0287899 A1 * | 12/2007 | Poupko | A61B 5/0535 600/383 |
| 2008/0269625 A1 | 10/2008 | Halperin | |
| 2008/0281301 A1 | 11/2008 | Deboer et al. | |
| 2009/0005703 A1 | 1/2009 | Fasciano | |
| 2009/0227965 A1 | 9/2009 | Wijesiriwardana | |
| 2010/0080794 A1 | 4/2010 | Tsuji et al. | |
| 2010/0120584 A1 | 5/2010 | Oshima et al. | |
| 2010/0121214 A1 | 5/2010 | Giftakis et al. | |
| 2011/0018706 A1 | 1/2011 | Egawa | |
| 2011/0040206 A1 * | 2/2011 | Burger | G01L 27/002 600/561 |
| 2011/0180709 A1 | 7/2011 | Craddock et al. | |
| 2011/0245629 A1 | 10/2011 | Giftakis et al. | |
| 2011/0263950 A1 * | 10/2011 | Larson | G16H 20/00 600/301 |
| 2011/0285516 A1 | 11/2011 | Ritter | |
| 2012/0029304 A1 | 2/2012 | Medina et al. | |
| 2012/0116485 A1 | 5/2012 | Burgmann | |
| 2012/0180567 A1 | 7/2012 | Mitsuaki | |
| 2013/0028942 A1 | 1/2013 | Surber et al. | |
| 2013/0041271 A1 * | 2/2013 | Ben-Ari | A61B 5/031 600/506 |
| 2013/0289422 A1 * | 10/2013 | Swoboda | A61B 5/021 600/490 |
| 2014/0027589 A1 | 1/2014 | Durgin | |
| 2014/0296687 A1 | 10/2014 | Irazoqui | |
| 2015/0018697 A1 | 1/2015 | Galea et al. | |
| 2015/0204744 A1 | 7/2015 | Heikki et al. | |
| 2015/0282753 A1 | 10/2015 | Mahdi et al. | |
| 2016/0022218 A1 * | 1/2016 | Hayes | A61B 5/117 600/595 |
| 2016/0235367 A1 | 8/2016 | Kolar et al. | |

FOREIGN PATENT DOCUMENTS

| | | |
|---|---|---|
| EP | 2081000 A | 7/2009 |
| EP | 2081000 A1 | 7/2009 |
| JP | 2004226294 A | 1/2003 |
| TW | 201 023 827 A1 | 7/2010 |
| WO | 9912607 A1 | 3/1999 |
| WO | 00/05771 A | 2/2000 |
| WO | 2006131855 A1 | 12/2004 |
| WO | 2010080794 A1 | 7/2010 |
| WO | 2013027027 A1 | 2/2013 |
| WO | 2015051770 A1 | 1/2015 |
| WO | 2011018706 A1 | 4/2015 |

OTHER PUBLICATIONS

Sorvoja, Hannu, "Noninvasive Blood Pressure Pulse Detection and Blood Pressure Determination," Acta Universitatis Ouluensis, Dec. 8, 2006, XP55240250, http://herkules.oulu.fi/isbn9514282728/sbn9514282728.pdf (retrieved on Jan. 11, 2016).
WIPO, International Search Report, in International Patent Application No. PCT/CZ2015/000113, filed on Oct. 1, 2015, dated Jan. 15, 2016.
WIPO, Written Opinion of the International Searching Authority, in International Patent Application No. PCT/CZ2015/000113, filed on Oct. 1, 2015, dated Jan. 15, 2016.
WIPO, Written Opinion, in International Application No. PCT/CZ2017/000041 filed Jun. 22, 2017, dated Oct. 17, 2017.
WIPO, International Search Report, in International Application No. PCT/CZ2017/000042 filed Jun. 22, 2017, dated Oct. 17, 2017.
WIPO, Written Opinion, in International Application No. PCT/CZ2017/000042 filed Jun. 22, 2017, dated Oct. 17, 2017.

* cited by examiner

DEVICE AND METHOD FOR MEASUREMENT OF VITAL FUNCTIONS, INCLUDING INTRACRANIAL PRESSURE, AND SYSTEM AND METHOD FOR COLLECTING DATA

CROSS-REFERENCE TO RELATED APPLICATIONS

This application is a continuation-in-part of U.S. patent application Ser. No. 16/304,157 filed Nov. 22, 2018, which is the National Phase of International Application PCT/CZ2017/000041 filed Jun. 22, 2017, which claims priority to Czech Application PV-2016-366 filed Jun. 22, 2016, and U.S. patent application Ser. No. 16/304,160 filed Nov. 22, 2018, which is the National Phase of International Application PCT/CZ2017/000042 filed Jun. 22, 2017, which claims priority to Czech Application PV-2016-366 filed Jun. 22, 2016, and U.S. patent application Ser. No. 15/518,402 filed Apr. 11, 2017, which is the National Phase of International Application PCT/CZ2015/000113 filed Oct. 1, 2015, which claims priority to Czech Application PV-2014-696 filed Oct. 11, 2014, the disclosures of which are incorporated herein by reference in their entirety.

TECHNICAL FIELD

The invention relates to a device and methods for monitoring patient's vital functions, such as respiratory and heart rate, and changes or arrhythmia thereof, and for use in the non-invasive measurement of intracranial pressure (ICP). A measuring device may be comprised of a mat with one or more sensors, which may include piezoelectric elements, and optionally, a device for R-wave detection in the ECG signal and invasive measuring device for determining arterial blood pressure (ABP). The invention also relates to a method of collecting or processing data from measuring devices, particularly from a plurality of measurement devices.

BACKGROUND OF THE INVENTION

Measurement of intracranial pressure (ICP) is very important for many clinical and diagnostic methods. ICP monitoring is crucial, namely for patients in a neurological department, and for polytrauma patients (e.g., after an accident). Increased ICP may indicate a serious life-threatening brain injury and practically always requires immediate surgery. High ICP may indicate, for example, a tumor, edema, acute liver failure and other life-threatening conditions. At the same time, low ICP is also physiologically dangerous, and is accompanied by nausea, migraines or visual impairment.

The most commonly used and the only accurate method of ICP measurement is currently an invasive method, during which pressure sensors are introduced to the brain tissue, which requires a physician to drill holes into the patient's skull. This method poses obvious risks for the patient in terms of health and following recovery, including the risk of infection.

Non-invasive methods known so far include measurements of intraocular pressure, otoacoustic emissions or tympanometry, visually stimulated evoked potentials or transcranial Doppler measurement of blood flow. Unfortunately, these methods do not guarantee sufficient accuracy and reliability of measurements.

One non-invasive method used for ICP measurement is described in US Patent Publication No. 2013289422, which includes a description of an ICP measuring device based on the relation between the pressure inside a carotid artery and the flow or flow speed of blood inside a carotid artery. The blood flow is measured using a piezoelectric sensor, which is attached to the carotid artery. Deduction of the ICP value is based on the shape of the pulse wave measured using the piezoelectric sensor.

Another approach to ICP measurement is described in U.S. Pat. No. 6,761,695, which describes a device for determining ICP comprising a pressure sensor attached to the head of a measured subject. The output of the sensor includes an ICP component and blood pressure component. A processor subtracts a blood pressure value from the output of the sensor in the same phase, which yields ICP.

Another possible approach and device for ICP monitoring are described in US Patent Publication No. 2009012430. This device is primarily intended for monitoring the bloodstream in the brain and the device can also be used to determine ICP. The publication discloses the injection of micro-bubbles into a patient's blood stream and followed by the assessment of a turbulent flow caused by the micro-bubbles. Vibrations are recorded by a field of accelerometers attached to the patient's head.

Another method for determining ICP is described in US Patent Publication No. 2010049082, which describes a procedure where, by using a number of vital parameters (i.e., $pCO_2$, $pO_2$, blood pressure, blood flow speed, etc.), it is possible to statistically assess an assumed ICP. This method includes two phases of a process: learning, during which data is collected, and simulation, during which data is assigned to potential ICP models. The disadvantage of this procedure is the relatively irrelevant output values that may not always correspond to the accuracy.

Unlike the above described procedures, the procedure described in U.S. Pat. No. 8,366,627 is significantly more complex and reliable. It uses a pressure sensor (i.e., tonometer or catheter) for blood pressure monitoring to calculate an ICP value. A calculation model includes parameters of resistance, submission, blood pressure and blood flow.

There are also solutions that employ a sensor attached to a patient's hand using a band, such as described in US Patent Publication No. 2013085400, which describes the sensor, which has an output signal that is processed and transferred using mathematical operations to a frequency spectrum and its components. These operations include, namely, Fourier transform, Fast Fourier transform or Wavelet transform.

Another alternative approach to the measurement of a brain parameter, not directly ICP, but a similar parameter (i.e., the blood pressure in the temporal artery), is described in US Patent Publication No. 2011213254, which describes a measuring device similar to headphones, which is in contact with the ear but a sensor is placed across a temporal artery, where it measures pulsation and deduces blood pressure in the temporal artery.

Various devices for monitoring various vital functions are known in the art. These monitoring devices are used especially in hospitals, mostly in intensive care units, but also in aftercare departments or in nursing homes. It is known to provide devices that do not contact a patient directly, which facilitates patient care, without the need for the patient's cooperation. Direct contact with the patient refers to various types of, for example, adhesive sensors or sensors that are inserted into the patient's body.

A majority of the known devices include a pad that incorporates one or more sensors of different types. These sensors can detect a change in force applied to the pad, for example, by means of various force sensors with offset measurement, strain gauges or sensors employing a piezoelectric effect. Furthermore, the sensors can also detect vibrations of the bed-deck caused by the patient, for example, by using various MEMS (micro-electromechanical system) sensors. The pad may be placed under the area where the patient is located, usually under the mattress.

A device employing appropriately configured strain gauges is described in U.S. Pat. No. 7,699,784. The disadvantage of this solution is that there is often an unwanted reaction caused by surrounding forces, due to the configuration of the strain gauges, so that the patient's breathing and heartbeat can be recorded.

Devices employing the principle of direct piezoelectric effect are utilized because of their low price and simplicity in measuring high-frequency vital functions, such as the heartbeat. An example of such a device is disclosed in U.S. Pat. No. 6,984,207. However, the device is not suitable for measuring low-frequency vital functions, such as breathing.

For measuring low-frequency vital functions, sensors for measuring offset are used, including, for example, capacity sensors utilizing capacity changes due to change in the size of the air gap between electrodes, as disclosed, for example, in International Publication No. WO2006131855.

A measuring device can also be as disclosed in International Publication No. WO2010080794, which describes a pad that is filled with fluid, and a pressure sensor that senses changes in pressure caused by a patient's breathing and pulse. A problem with this solution is in connection with the production complexity of the special pad filled with fluid.

A device can also employ a video signal evaluation principle, as disclosed in International Publication No. WO2013027027, where it is possible to evaluate some vital functions on the basis of a light intensity ratio of two different wavelengths reflected from a patient's skin. However, this principle is inaccurate and very difficult to perform in poor lighting conditions.

A device can also be formed by mattresses into which a sensor is inserted, as disclosed in U.S. Pat. No. 7,652,581. However, this method is disadvantageous due to the high price of the mattress adapted for this purpose.

Remote monitoring has been used in health services for a long time. It is a very good tool for saving time and human resources. However, it is crucial to ensure that remote monitoring is carried out efficiently and mainly without errors.

There is currently a challenging task to collect and process reliable data from measurement devices, particularly, a plurality of measurement devices simultaneously, and more particularly, a plurality of devices with sensors for monitoring various vital signs. Conventional apparatuses typically comprise several sensors, which measure external mechanical or chemical states of surroundings of the sensors, and by various electromechanical features, provide measurements of the electrical physical quantities, such as resistance, capacitance, amperage, and so on. Measured data is sent as an analog signal to a control unit. The analog signal has several disadvantages, such as a low resistance to electromagnetic interference, and the signal can be compromised. Therefore, it is necessary to use wires that protect the signal from such external disturbances. Furthermore, in conventional devices, the signal needs to be modulated in the sensor and demodulated prior to entering a control unit. Microprocessors are the most commonly used control units in such apparatuses.

Information is usually collected from a plurality of sensors in such measurement devices using a classical topology of an electrical circuit, such as Y, T or star topology. In some cases, the star-mesh topology can also be used. However, this topology requires the use of a separate connection for each apparatus. Usually, a signal wire (or more generally, a signal path) and a data signal path have to be employed. A connection of this type is quite expensive. It should be kept in mind that, in a typical healthcare application, such as, in hospital beds, several apparatuses for measuring various states are provided. Firstly, vital functions of patients are to be monitored. As mentioned above, such vital functions are most commonly heartbeat and respiration, although other functions, such as apnea, intracranial pressure or peristalsis, can be measured. A plurality of other sensor apparatuses is also used in hospital beds, stretchers or chairs. Such apparatuses indicate, for example, the weight status of the patient, the state of the bed, the state of bed actuators, and so on. There are various apparatuses in each room and most of them are remotely monitored from a nurse's station. Therefore, in the case of star topology, every single apparatus has to be connected separately with the control unit of a measuring device, wherein the collected data is further sent to a server or a readable monitor.

Prior art medical data collection systems do not provide safe collection of the measured data. Moreover, a large amount of hardware equipment is needed for providing communication between sensors and the control unit.

SUMMARY OF THE INVENTION

The present invention relates to a device and method for monitoring a patient's vital functions, and for use in the non-invasive measurement of intracranial pressure (ICP) may be solved by a device, which may be comprised of a measuring mat, which may be configured to support at least one sensor, preferably a piezoelectric sensor. The mat and/or sensor may be configured for placement under or proximate to the head of a patient. Other optional components of this device include a device for heart rate measurement and a sensor for invasive measurement or arterial blood pressure (ABP).

The sensor is configured to sense micro movements and/or mechanical vibrations, particularly, in the head, which are caused by the hemodynamics of the patient's blood circulation, as a result of a pulse wave that is reflected in the bloodstream inside the patient's head. Furthermore, ECG can be used to detect a R-wave. The device may also employ a sensor for invasive measurement of arterial blood pressure (ABP). ICP may be calculated from a relation using a time delay of a reflected pulse wave in relation to the moment of a detected R-wave.

An experimental study discovered and verified that relative changes of IPC may be measured even without the necessity to use invasive ABP measurement or to detect the R-wave. The method is based on the detection of a sequence of pulse waves and their reflection in relation to individual pulses and their mutual time delay.

The invention also relates to a device for monitoring a patient's vital functions, which may be comprised of a computing unit and a piezoelectric transducer. The device may comprise a measuring electrode coupled to a board forming a measuring capacitor together with a piezoelectric transducer. The piezoelectric transducer and the measuring capacitor may be electrically connected to or otherwise in communication with the computing unit. The piezoelectric transducer is deformable and is supported in relation to the board in at least two places so that a flexible part of the piezoelectric transducer is located between these places. A place for a bent portion of the piezoelectric transducer is achieved, for example, by a saucer-type shape of the piezoelectric transducer or by placing the piezoelectric transducer on an elevated place of the board or through a hole in the board. This advantage is utilized for mechanical simplification of the design and simultaneously for a reduction of failure rate.

Another aspect of the invention relates to a medical data collection system. The system may comprise a control unit and a plurality of measuring devices, wherein the measuring devices are connected in series via data signal paths. A feature of the data collection system is that the control unit may comprise a trigger and the trigger may be connected to each measuring device via a trigger signal path. Preferably, the measuring device comprises a piezoelectric and capacity sensor for vital functions. In a preferred embodiment, the measuring device includes the computing unit.

The invention is also related to a method for collecting medical data in a data collection system. The method may introduce a set of logical operations, which may be necessary for data acquisition. First, the trigger may initiate data collection by transmitting a time-synchronizing impulse into measuring devices $A_k$. Second, a measuring device $A_N$ may transmit a data package of the measuring device $A_N$ to another measuring device $A_{N-1}$ and measuring devices $A_2$-$A_{N-1}$ simultaneously receive data packages from a measuring device $A_{k+1}$ and transmit their own data packages to another measuring device $A_N$. Simultaneously, the measuring device $A_1$ receives the data package from the measuring device $A_2$ and transmits its own data package to the control unit.

In another step, measuring devices $A_2$-$A_{N-2}$ may simultaneously receive the data packages from a measuring device $A_{k+2}$ and transmit previously received data packages to the measuring device $A_{k-1}$. At the end of this process, the measuring device $A_1$ receives a data package from the measuring device $A_2$ and transmits a previously received data package to the control unit, and a cascade receiving and transmitting of data packages continues until the data package from the measuring device $A_N$ is transmitted to the control unit by the measuring element $A_1$.

Simplification of entire process lies in the fact that each measuring element $A_k$ transmits its own data to the measuring device $A_{k-1}$ and receives data from the measuring device $A_{k+1}$. The process repeats until the measuring device $A_1$ transmits N data packages to the control unit. The process may be utilized to collect and process information about a patient's vital functions.

Various advantages of this invention will become apparent to those skilled in the art from the following detailed description of the preferred embodiment, when read in light of the accompanying drawings.

DETAILED DESCRIPTION OF THE PREFERRED EMBODIMENT

Figure 1A:
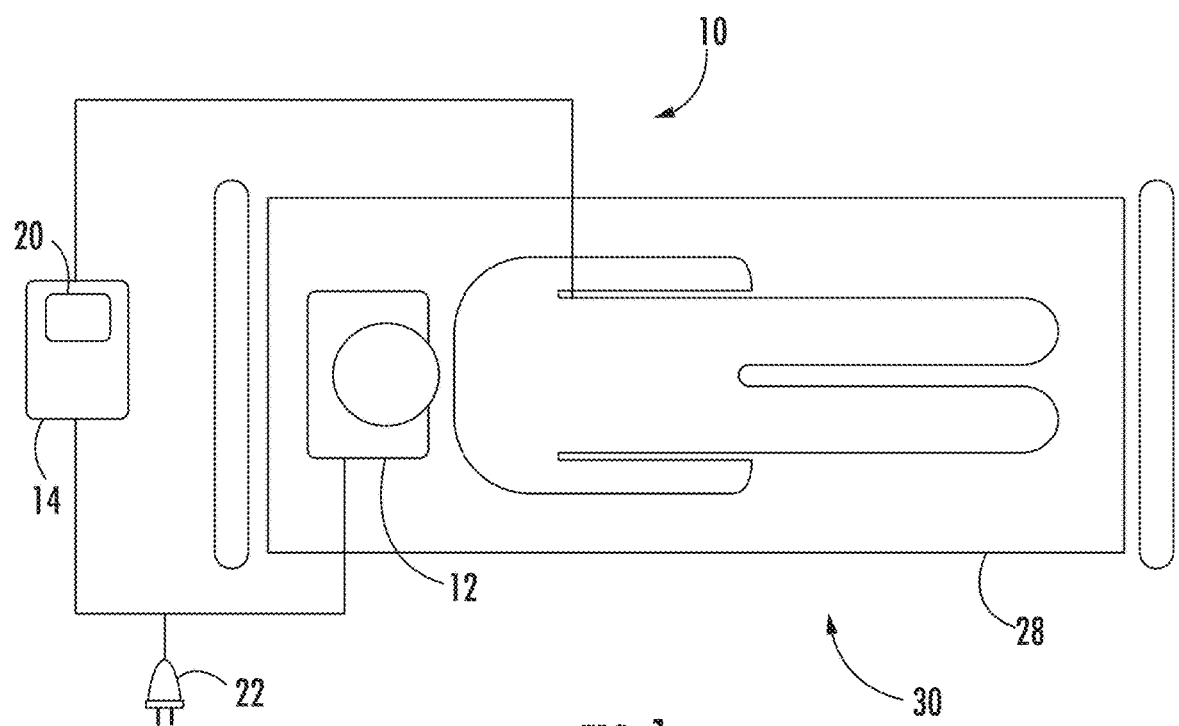
FIGS. 1a, 1b and 1c schematically represent an exemplary device for non-invasive measurement of intracranial pressure (ICP) and its components.
Figure 1B:
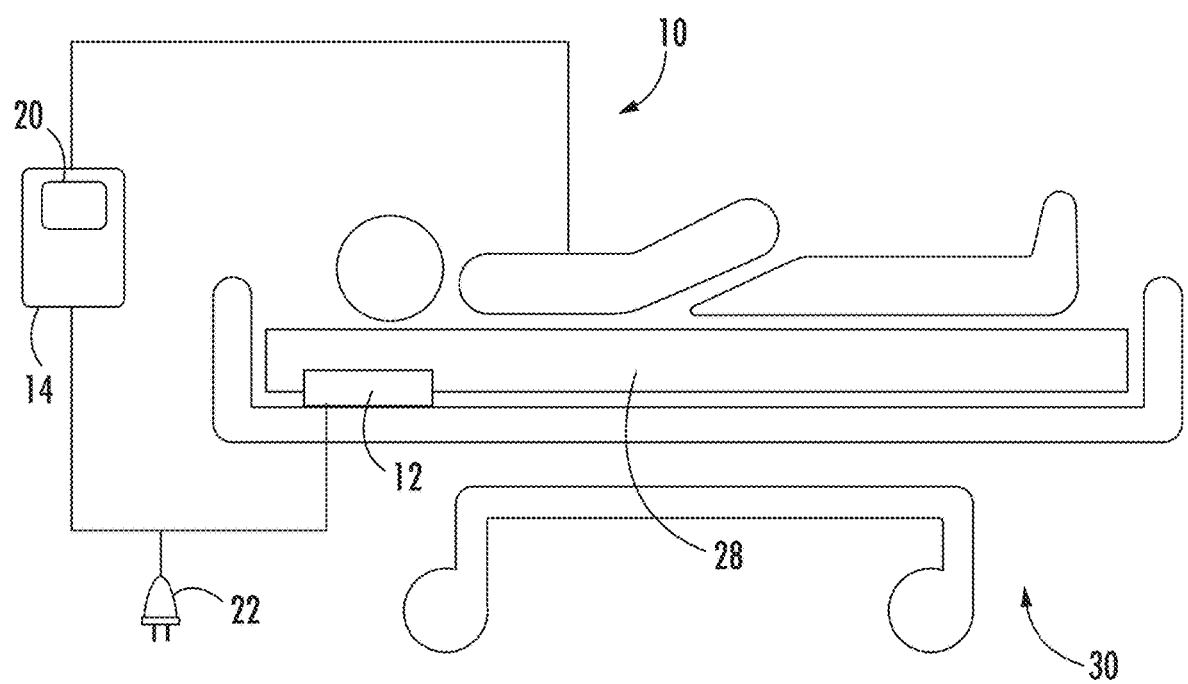
Figure 1C:
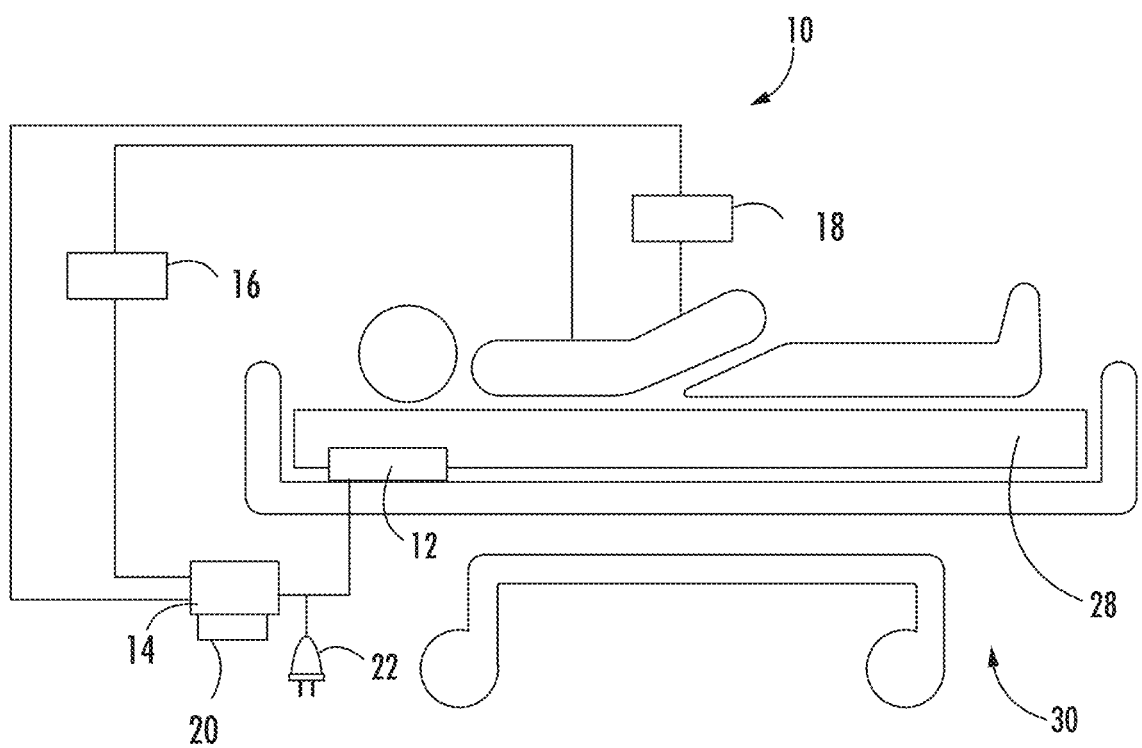

Now, with reference to FIGS. 1a, 1b and 1c, there is illustrated a device 10 for non-invasive monitoring of intracranial pressure (ICP). The device 10 may include a measuring mat 12, a processor unit 14, a device 16 for measuring electrical activity of the heart (e.g., an electrocardiogram (ECG)), a device 18 for invasive measurement of arterial blood pressure (ABP), a display unit 20 and a network connector 22. At least one of the devices 16, 18 for monitoring electrical activity of the heart or for invasive measurement of arterial blood pressure (ABP) may be a reference device. For the purposes of this description, the terms sensing, measuring, monitoring, detecting, recording and the like may be used interchangeably, without limitation to the particular term used.

The measuring mat 12 may be in the form of a relatively flat piece of material, or a substantially planar member, having a limited thickness, and configured for placement under a patient's head, preferably, without detection. The mat 12 may support at least one sensor, which may be in the form of a piezoelectric sensor 24, or some other suitable sensor. The mat 12 may be located in a suitable position under or proximate to the patient's head, for example, in a head support, as shown in FIG. 1a. It is suitable to use a piezoelectric sensor 24 with a third conductive capacity electrode, as described hereinbelow. Such a sensor may provide additional information about the patient, such as, for example, information about other vital signals (e.g., respiration, pulse or heartbeat, ECG, etc.) and the patient's weight. The head support may include a retention device, such as a profile in a mattress, or a belt or strap, which may be adjusted to keep the patient's head in one position and to prevent self-positioning of the patient's head to the sides. It is suitable to cover the measuring mat 12 with a material that ensures better comfort during handling and which has better hygienic properties. The measuring mat 12 may be placed under a mattress 28 on a hospital bed 30 under the patient's head, as depicted in FIGS. 1b and 1c.

Figure 2:
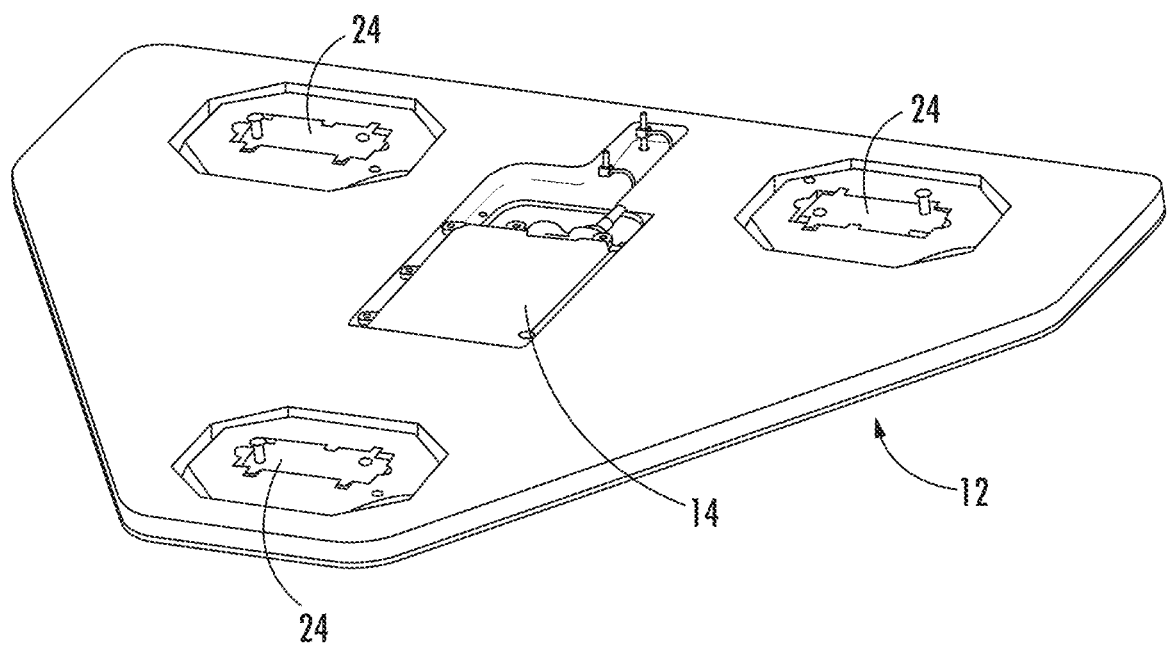
FIG. 2 shows a measuring mat for use with the device.

An arrangement of a plurality of sensors 24 may be supported by the measuring mat 12, as indicated in FIG. 2. The mat 12 may comprise one or more pockets for receiving sensors 24. The mat 12 may be dimensioned to support the sensors 24 within the pockets, preferably recessed within the pockets or flush with a surface of the mat 12 surrounding the sensors 24. The processor unit 14 may likewise fit within a pocket formed in the mat 12 and may be supported within the mat 12, preferably recessed within the pocket or flush with the surface of the mat 12 surrounding the processor unit 14. The mat 12 may be further configured to support wiring for electrically connecting the processor unit 14 to the sensor 24, if such wiring is desired. The mat 12 may be configured to support a plurality of sensors 24, so that the sensors 24 are positioned at locations around or about the patient's head (e.g., with the patient's head above the center of the mat 12). The mat 12 may be in the form of a flexible plastic material and may be sufficiently sized with a thickness that is limited so as not to noticeably protrude into a pillow or a mattress when placed under the same. For purposes of monitoring long-term health trends, one sensor 24 may be fully sufficient, particularly if the signals coming from a plurality of sensors 24 are similar. Although three sensors 24 are shown and may be suitable for positioning around the patient's head, the invention can be carried out with any suitable number of sensors 24. Mechanical manifestations of the bloodstream dynamics in alternative embodiments may be sensed using, for instance, a piezoresistive sensor, a tensometer or an accelerometer. Alternatively, the bloodstream dynamics may be monitored optically or using a different suitable sensor or method.

It should be appreciated that one or more sensors 24 may be supported in relation to the patient's head without the use of the mat 12. However, the use of a mat 12 aids in managing the position of a plurality of sensors 24 (i.e., maintaining the sensors 24 in desired positions). The sensors 24 are also configured to be supported remotely from the patient's head, without physically contacting the patient's head directly, while sensing the mechanical manifestations of the patient's head.

As mentioned above, the measuring device 10 may include a device 16 for measurement of electrical activity of the heart, such as an electrocardiogram (ECG), and a device 18 for invasive measurement of arterial blood pressure (ABP). It may be suitable to extend these functions by a standard patient monitor, wherein the measuring device 10 is configured to be connected to a conventional patient monitor of a hospital system, which may regularly monitor all the patients by a conventional method, particularly, patients in an intensive care unit with data output. The output signal is preferably digital. However, an analog signal can also be used. If an analog output signal is used, it may be necessary to use an A/D converter (an A/D converter may form a part of the processor unit 14, which produces the digital output data shown in FIGS. 7a and 7b). Those skilled in the art of processing analog signals can design several possible connections of the A/D converter in order for the processor unit 14 to be able to correctly assess signals and calculate ICP. At the same time, those skilled in the art of bio signals can use other suitable equipment for monitoring of electric activities of the heart, such as vector cardiograph (VCG). Alternatively, ballistocardiograph signals can also be used.

In an alternative embodiment, it is possible to use non-invasive ABP measurement. However, a preferred embodiment assumes non-stop monitoring of the patient in an intensive care unit or in an anesthetics and resuscitation department, where ABP is normally measured invasively. For this reason, the device 10 is described, by example, using an invasive device 18 for measuring ABP.

As stated above, the processor unit 14 may be located inside the measuring mat 12, as indicated in FIG. 2. In an alternative embodiment (FIGS. 1a through 1c), the processor unit 14 can be located outside or apart from the measuring mat 12, as a separate module, with an independent display unit 20. The device 16 for monitoring heart (e.g., electrocardiogram, vectorcardiogram and ballistocardiogram) activity and the invasive device 18 for measuring ABP may be separate. All recorded signals, which are synchronized, may then be transferred to the processor unit 14. In an alternative embodiment, the processor unit 14 may be a part of a specialized patient monitor (e.g., a vital functions monitor described herein). In this case, the signal from the measuring mat 12 may be transmitted directly to the specialized patient monitor, where the processor unit 14 assesses ICP and displays the ICP on a screen of the patient's monitor. The processor unit 14 may be connected to one or more sensors 24, the device 16 for monitoring heart activity and/or the device 18 for measuring ABP. Signals from the sensors and devices 24, 16 and 18 may be processed by the processor unit 14 and the processed data may then be sent to the display unit 20. As mentioned above, the display unit 20 may be provided separately, as shown in FIGS. 1a through 1c, or the processor unit 14 may be a part of a patient monitor. In this case, data may be transmitted to a connector for an external output signal. The display unit 20 may display current values, trends, mean values, ICP, ECG, ABP, and other vital functions of the patient in the case of a patient monitor (e.g., the vital functions monitor described herein). The display unit 20 can be advantageously connected to a hospital system for collection of patient data. That is to say, the display unit 20 can be wired or wirelessly connected to a monitoring device of a conventional hospital system (i.e., a standard hospital monitoring system, to which the device 10 or display unit 20 can be connected). The display unit 20 can also display critical states, when the value of a displayed parameter is outside predefined limit values. Limit values can be adjusted manually in accordance with the individual needs of the patient.

Critical conditions may also be detected if the current ICP value deviates from a long-term average. Notification of these conditions may be sent to a hospital system for collection of patient data, which may then further distribute the information. Alternatively, information about critical conditions may be sent directly to medical staff.

Method I

Figure 3:
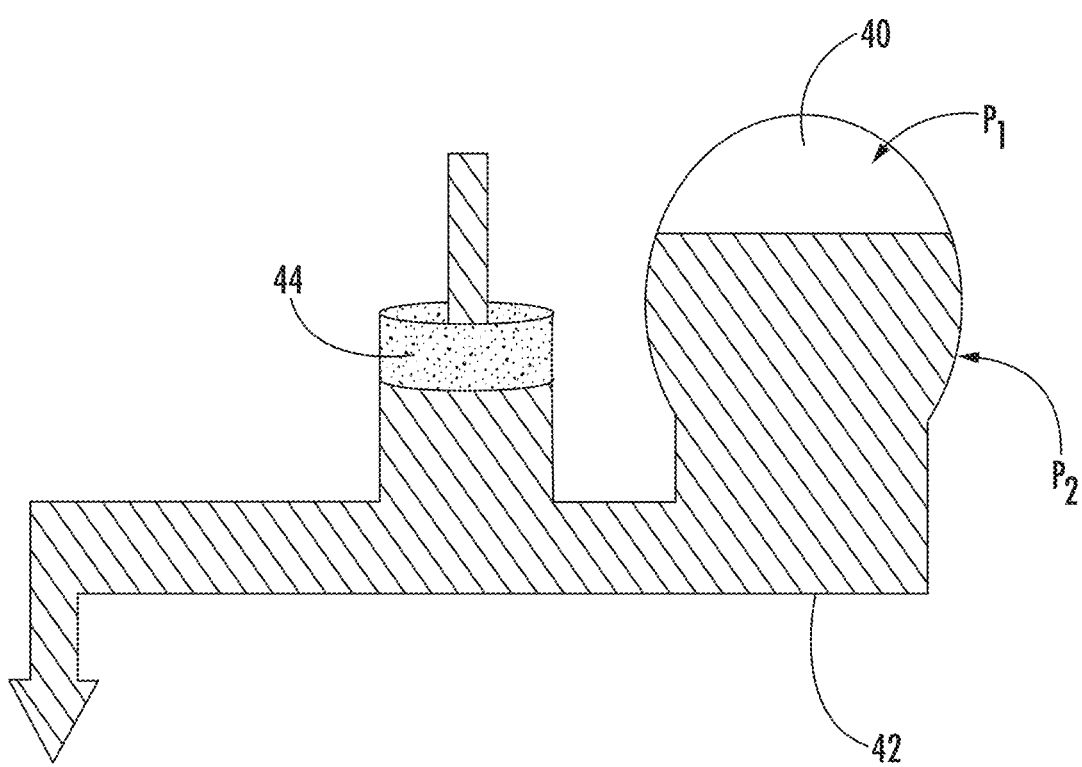
FIG. 3 schematically depicts a vascular system.

A method for calculating a patient's Intracranial pressure (ICP) may be based on an existing relation between pressure inside the cranial cavity 40 and bloodstream hemodynamics 42, as schematically represented in FIG. 3. This mutual relationship is manifested, for example, by synchronous changes of ICP and heart activity (as described, for instance, in an article by Wagshul M. et al. entitled "The pulsating brain: A review of experimental and clinical studies of intracranial pulsatility", published by Fluids and Barriers of the CNS, 8, Article 5 (2011)). From a mechanical point of view, synchronized ICP and arterial blood pressure (ABP) oscillation occurs and it is caused by changes of ABP as well as the volume of blood in brain arteries and vessels. The brain volume changes proportionally with ABP. If the brain were not located in the cranial cavity 40, clear pulsations would be visible. In fact, the brain is stored in cerebrospinal fluid, an incompressible fluid, and is enclosed in a hard shell (i.e. the skull). Increased ABP leads to brain swelling and to higher ICP. When the ABP and the ICP are locally balanced, the brain cannot increase its volume anymore, as it cannot receive any more blood due to the fact that the pressure of blood entering the brain is no longer higher than the ICP, as reflected by the entering pulse wave. This situation is schematically represented in FIG. 3, where the ICP corresponds to $P_1$ and the ABP corresponds to $P_2$. The heart 44 is represented as a pumping piston that pumps blood.

This situation is commonly described using the simple Windkessel hydrodynamic model. In common practice, the Windkessel model is used to determine the aorta elasticity. This model is solved using differential equations, where the heart 44 is represented as the pulse source and input parameters represent the flexibility of arteries and vascular resistance. This model enables the calculation and description of a pulse wave. The Windkessel model is described in detail, for instance, in an article by Westerhof N. et al. entitled "The arterial Windkessel, published by Med Biol Eng Comput, Vol. 47, Issue 2 (2009) (doi 10.1007/s11517-008-0359-2 (2008)).

An analytical solution of these differential equations is impossible. They need to be solved numerically. This model is used for pulse wave reflection in the head. On the basis of physical considerations, it may be deduced that the elasticity of the bloodstream in the brain C is inversely proportional to ICP. The following equation I therefore applies:

$$ICP \sim \frac{1}{C} \qquad (I)$$

Figure 6:
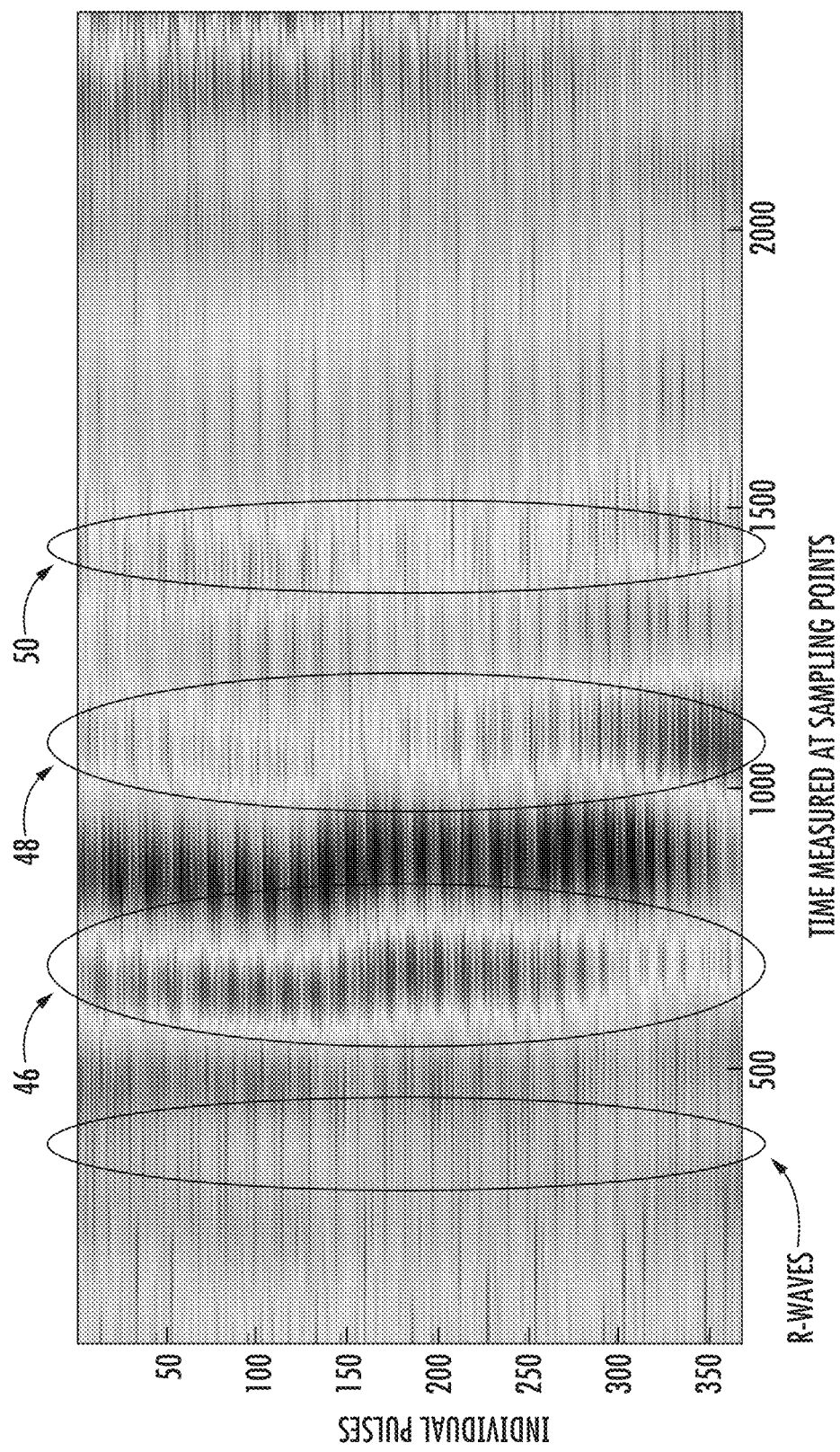
FIG. 6 shows a data matrix of a signal from the measuring mat.

From Newton's laws of motion, specifically from the law of inertia, it follows that the reflection of a pulse wave is accompanied by a mechanical movement of the head, which is measurable using the above described sensor, which may be supported by the measuring mat 12. These mechanical head movements are depicted in FIG. 6, where they are identified in areas 46, 48 and 50.

The beginning of the mechanical pulse, which corresponds to a R-wave in an ECG signal, and $T_1$ of the pulse wave reflection (i.e., mechanical head movement in area 48) determines the time delay T between the R-wave and mechanical movement of the head in area 48. In the equation for the Windkessel model, the R-wave represents the source part of the equation, which describes the activity of the piston pump corresponding to the heart 44. Blood is pumped into the brain under a pressure that equals the ABP. The pressure of the brain tissue and cerebrospinal fluid that equals the ICP acts against the ABP. The difference between the ICP and the ABP is called the cerebral perfusion pressure (CPP). The time delay T between the R-wave and reflection of the pulse wave in the head is then solved as a Winkessel equation using the relation II:

$$CPP \sim -A \cdot \log(T - T_0) \qquad (II)$$

where A is an empirically determined constant, $T_0$ is the time that would correspond to the reflection time at infinite intracranial pressure. The time when the pulse wave appears on the carotid artery may be used as $T_0$.

In the following steps, ICP is calculated using known values for ABP and CPP. This calculation is done using equation III:

$$ABP - CPP = ICP \qquad (III)$$

Figure 4:
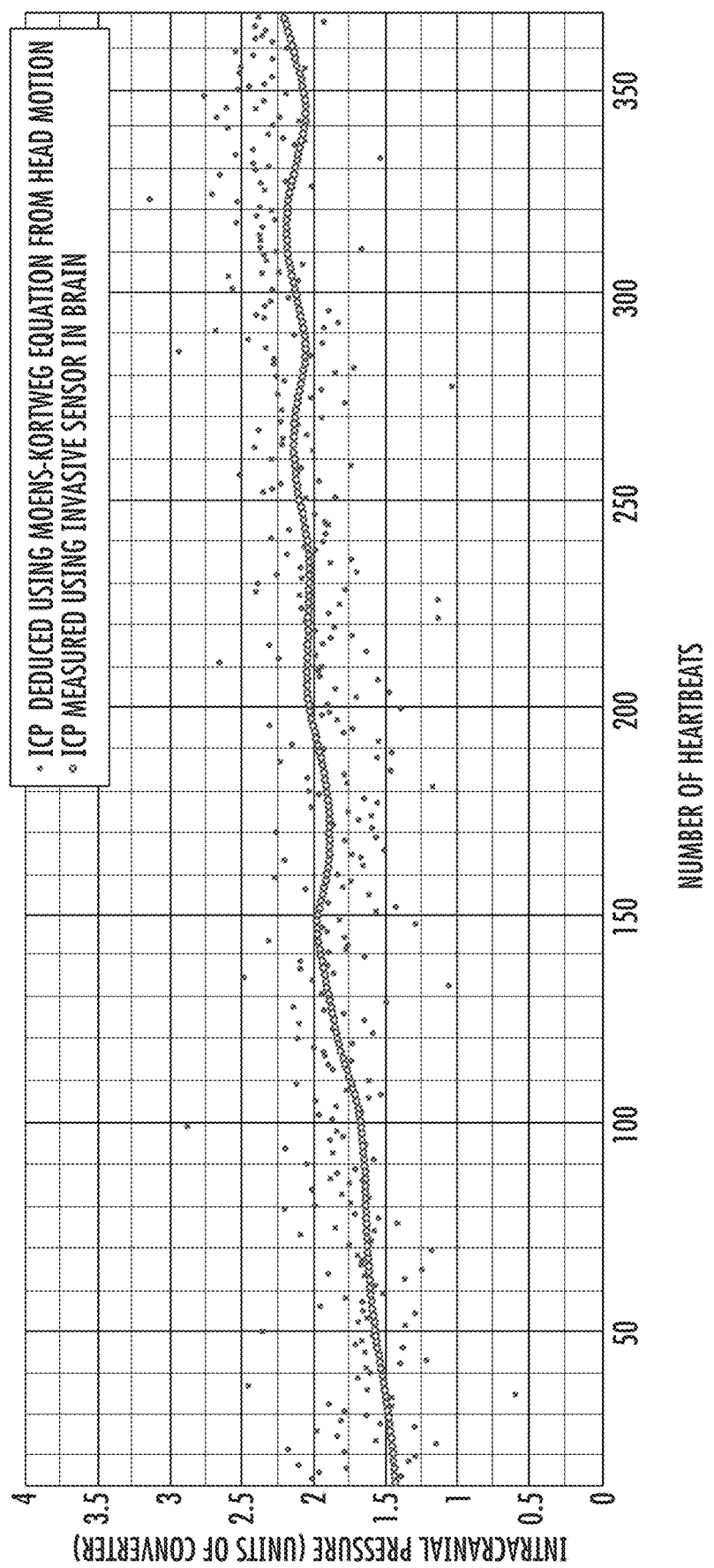
FIG. 4 shows a graph that represents a non-invasive measurement of ICP using the device according to the invention in comparison with an invasive measurement of ICP.

As is visible from FIG. 4, the trend of results measured using the described method is similar to the trend of results using an invasive method with intracranial sensors. The time delay T between the head movement and the ICP was calculated using equations II and III.

The non-invasive method was verified in several tested subjects (i.e., patients). The verification equipment included an A/D converter, which was connected to the output of an invasive sensor for ICP measurement, an output signal from an ECG monitoring device 16 and a signal from the measuring mat 12 and/or sensor 24 under the patient's head. All signals were sampled at frequency of 2 kHz.

Figure 5:
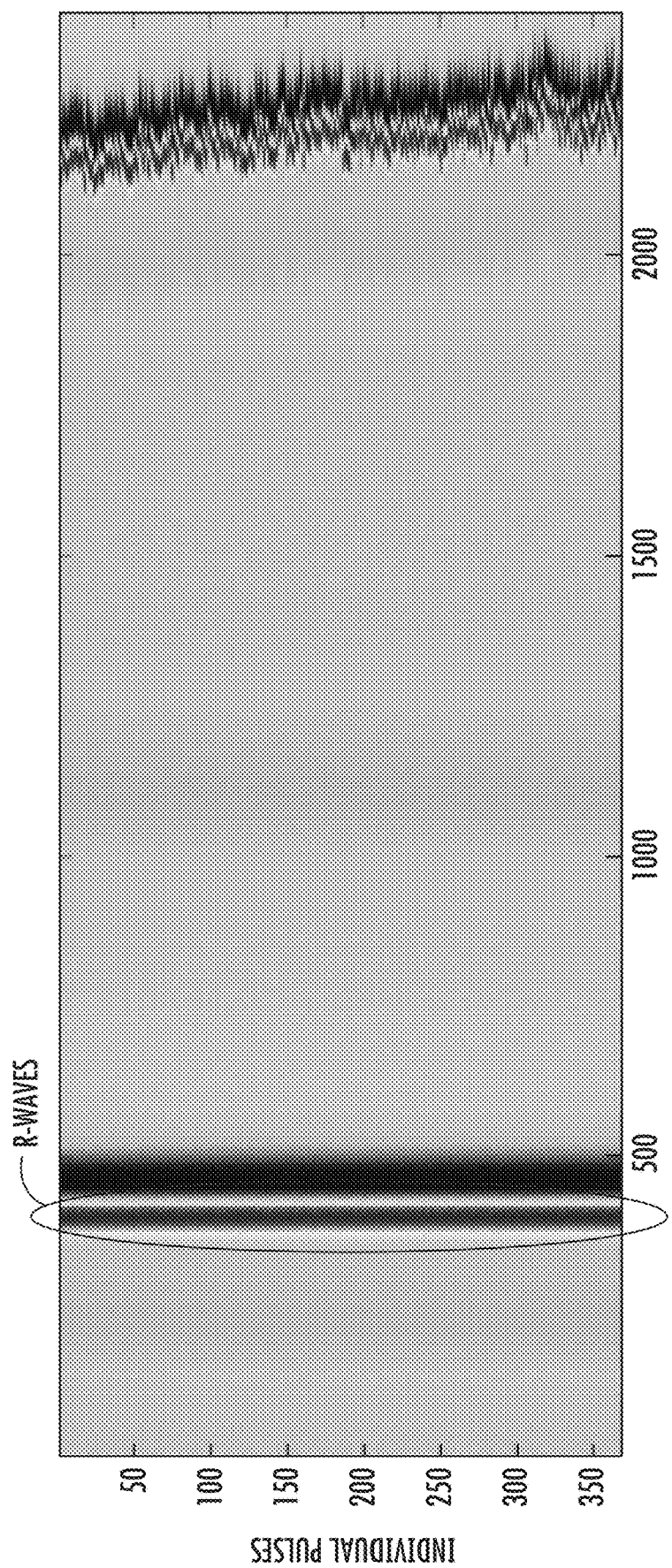
FIG. 5 shows a data matrix of an electrocardiogram (ECG) signal with synchronized R-waves.

R-waves of the QRS complex (including the Q wave, R wave and S wave) were localized in the obtained ECG signal using standard procedures and the signal was then divided by R-waves into individual sections so that each section covered a time interval ($R_n - 400$, $R_n + 2000$), where $R_n$ is the nth R-wave and time is measured on sampling points (i.e., each such interval contains a section of signals that start at a value of 400 sampling points (0.2 s) before the R-wave and end at a value of 2000 sampling points (1 s) after the R-wave). The time range ($R_n - 400$, $R_n + 2000$) was selected for the verification experiment in order to ensure with absolute certainty that the given interval covers two consecutive R-waves. When these intervals are ordered under each other so that the first R-wave is synchronized in time, a data matrix for each measured channel is provided, as shown in FIG. 5.

Figure 7A:
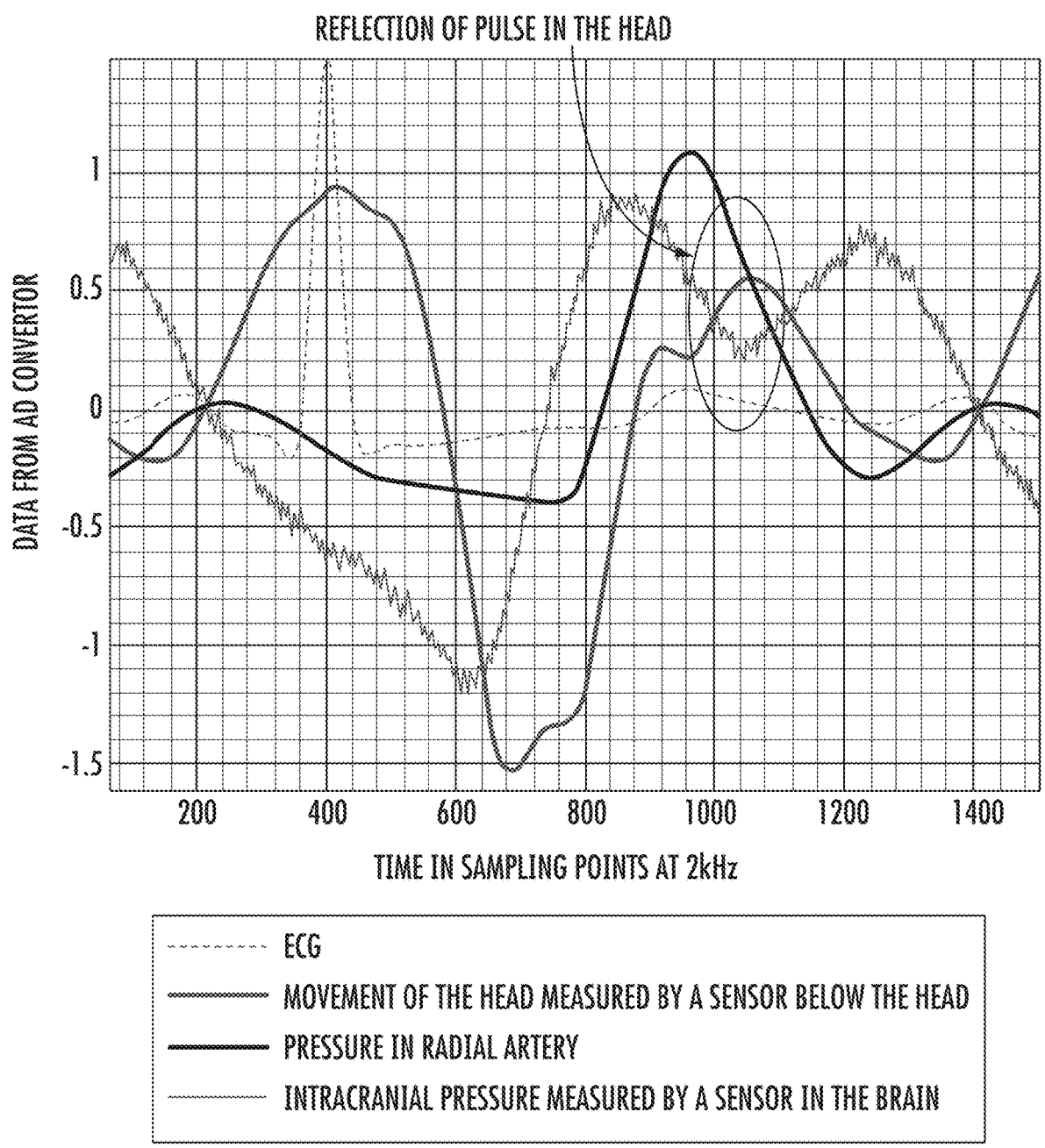
FIGS. 7a and 7b shows a time match of an ICP peak with a peak of head movement.
Figure 7B:
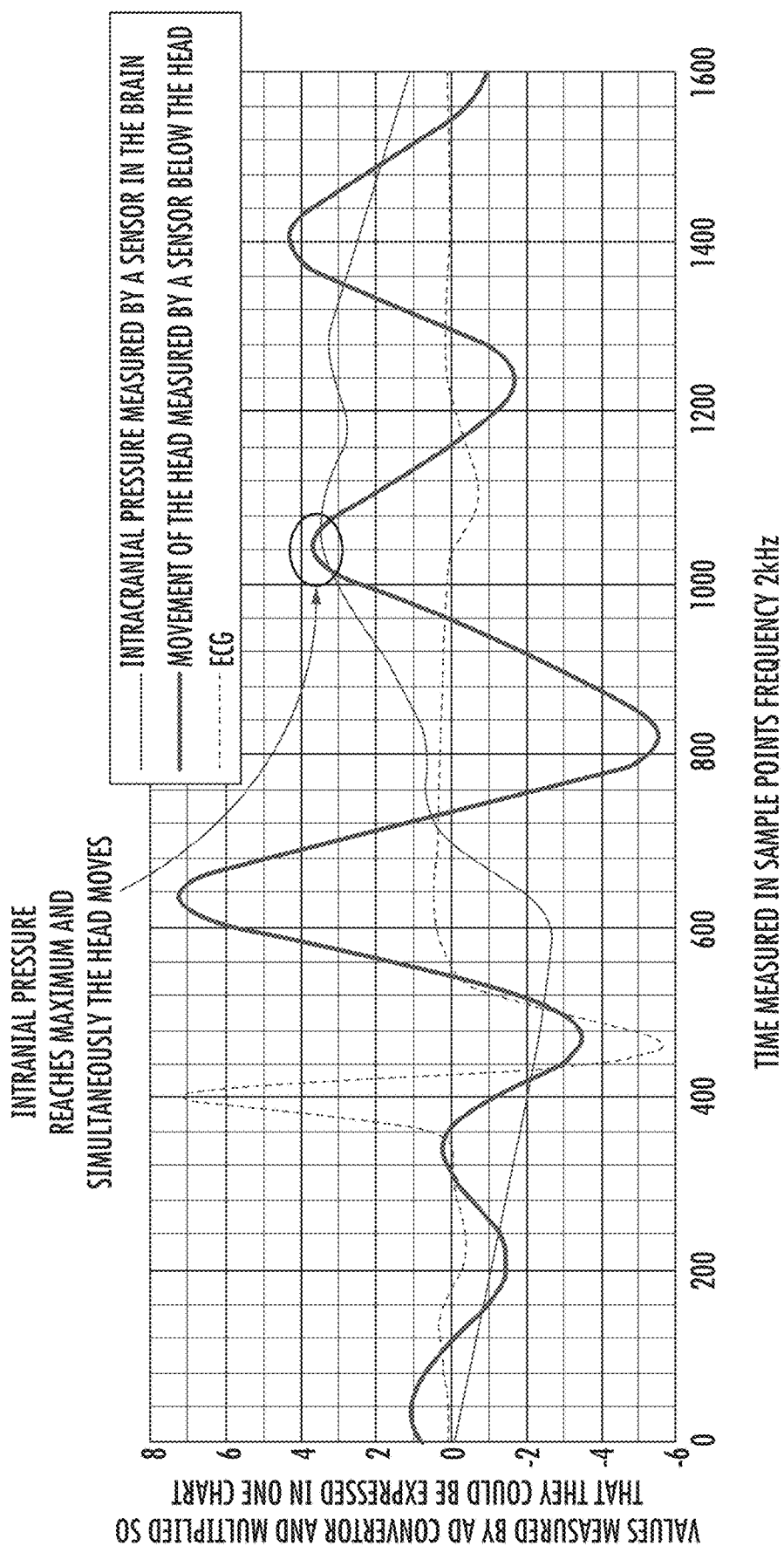

A signal from the piezoelectric sensor 24 corresponding to ordered R-waves is depicted in FIG. 6, which shows individual reflections of the pulse wave in the head represented by areas 46, 48 and 50, caused by changes of intracranial and arterial pressure. For purposes of this method, area 48 is the most important. It may be assumed that, during the time of ten consecutive R-waves, the ABP and the ICP remain constant and the circulation system during these ten consecutive heart cycles remains stable. FIGS. 7a and 7b show different values obtained from two different patients. As is clear from FIGS. 7a and 7b, the time of maximum values of intracranial pressure matches the mechanical movement of the head in area 48. Data from the A/D converter was multiplied by suitable constants so that they can be displayed in a single graph.

Method II

Another method for calculating a patient's intracranial pressure (ICP) uses a device 10 for non-invasive monitoring ICP, like the device described above, which includes one or more sensors 24 (which may be supported by the measuring mat 12), a processor unit 14, a display unit 20, a network connector 22 and devices for measuring a parameter related to arterial blood pressure (ABP), which may be a device 16 for sensing, electrical activity of the heart and/or a device 18 for invasive measurement of arterial blood pressure.

All calculations and relations are explained with reference to a single listening cycle for the sake of simplicity. In terms of time, this concerns the area between two R-waves, where the first R-wave is considered the start of action $T_0$. Practically immediately after the R-wave, a whole spectrum of mechanical actions occurs in the bloodstream and they are reflected in the final signal in the form of oscillations, peaks, or the like. For further processing, it is necessary to identify only significant peaks.

One of these key peaks corresponds to the instant when the pulse wave is reflected from the patient's head. This time is identified as $T_1$ and is determined using the maximum value located in a corresponding area 56, shown in FIG. 8. Blood is pumped into the brain at a pressure that equals the ABP. The pressure of the brain tissue and cerebrospinal fluid that equals the ICP acts against the ABP. There is a clear analogy with, for example, inflating a balloon using pressure $P_2$ inside a hollow sphere with a solid wall (similar to FIG. 3 referenced above). If the balloon is inflated at a low pressure $P_2$, the balloon will eventually not increase in volume. If the balloon is inflated at a high pressure $P_2$, the balloon will take longer to inflate and the volume of air in the balloon will become greater, proportional to the pressure $P_2$. On the other hand, if there is a high pressure $P_1$ acting against pressure $P_2$ inflating the balloon, the balloon will stop inflating as pressures $P_1$ and $P_2$ become equal. It follows from this development and the analogical model that time $T_1$ is inversely proportional to the ICP. Equation IV therefore applies:

$$T_1 \sim e^{-ICP} \qquad (IV)$$

Figure 8:
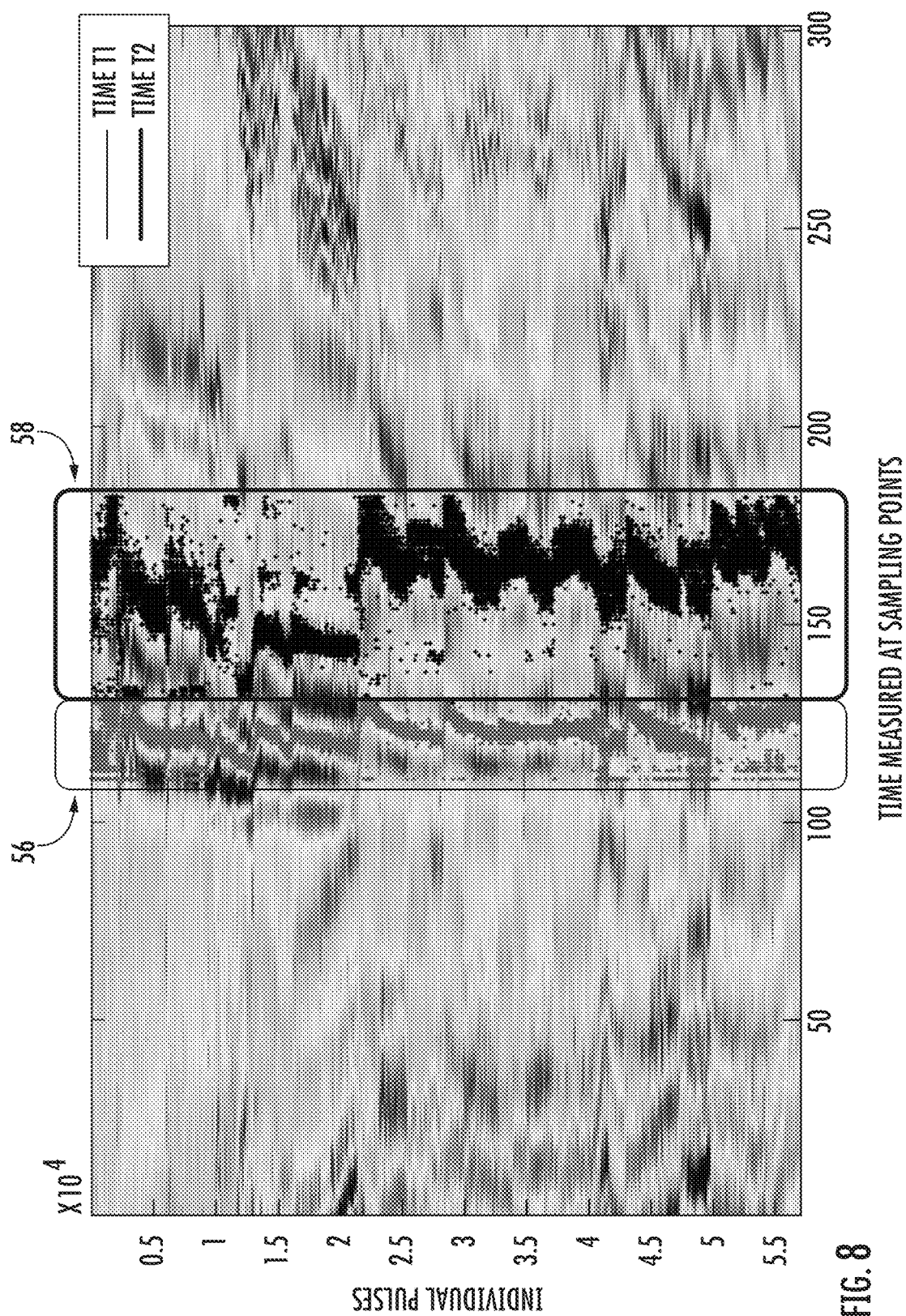
FIG. 8 represents a data matrix of ECG signal with emphasized mechanical manifestations.

A second key parameter is related to the closing of the aortic valve. This phenomenon is mechanically significant, and it is known as the water hammer. This time is referred to as $T_2$. In FIG. 8, this moment corresponds to the peak in a corresponding area 58. It has been experimentally verified that this time correlates with the time when the pressure wave reaches the device 18 for invasive measurement of the ABP.

In accordance with the Moens-Korteweb equation, which models the relationship between wave speed or pulse wave velocity (PWV) and the incremental elastic modulus of the arterial wall or its distensibility, in the following form (equation V):

$$ABP = \alpha \cdot \ln\left(\frac{b}{\left(\frac{d}{PWV} - c\right)^2} - 1\right) \quad (V)$$

ABP refers to the arterial blood pressure, PWV is the pulse wave velocity, and a, b, c and d are certain constants. It holds that $T_2$, when the pulse wave reaches the place of measurement of the ABP, is inversely proportional to pressure (i.e., the higher the pressure, the slower the time of arrival of the pressure wave).

The specific equation for determining $T_2$ corresponds to the following equation (VI), as is specified in an article by F. Studnicka: entitled "Analysis of biomedical signals using differential geometry invariants", published by Acta Physica Polonica A, Vol. 120, page A-154 (2011):

$$\ln(T_2) \sim -ABP \quad (VI)$$

Some of other results following from the Moens-Kortweg equation can be found for example in an article by E. Pinheiro, O. Postolache, P. Girao entitled "Non-Intrusive Device for Real-Time Circulatory System Assessment with Advanced Signal Processing Capabilities", published by Measurement Science Review, Vol. 10, No. 5 (2010).

Time $T_0$ is introduced to the Windkessel model. This time is related to the instant the pulse wave reflects from the head. From the model, it follows that the ICP is proportionate to the logarithm of differences of times $T_1$ and $T_0$. Time $T_0$ can be substituted by the time when the pulse wave goes through the carotid artery. This time correlates to the time when the pulse wave reaches the radial artery (i.e., the place where standard invasive measurements of the ABP are taken using the device 18). Again, $T_0$ in accordance with the Moens-Kortweg equation is inversely proportional to the ABP.

The time $T_0$ cannot be experimentally defined. However, it was possible to experimentally verify the correlation between $T_0$ and $T_2$. From the description above, it follows that it is not necessary to measure the ABP, but instead only the time at which the pulse wave appears in the radial artery. This measurement can be carried out using a sensor for invasive measurement of the ABP, as these measurements are carried out standardly in intensive care units. However, in order to detect relative changes of the ICP, only data from the measuring mat 12 (or sensor 24) is required, as documented in an article by F. Studnicka entitled "Analysis of biomedical signals using differential geometry invariants", published by Acta Physica Polonica A, vol. 120, page A-154 (2011).

From the equations stated above (IV and VI) and from the previous paragraph, we obtain equation VII:

$$ICP \sim \ln|(T_2 - T_1)| \quad (VII)$$

This equation has been experimentally verified on tested subjects, even for situations when the head position changes.

On the basis of the description above, it is clear that, for monitoring of relative changes of the ICP, it is possible to use the ICP monitoring device, including only a measuring mat (or sensor) and a processor unit.

To measure absolute ICP values, the device needs to include a measuring mat (or sensor), processor unit and either a device 16 for measurement of electric activities of the heart or a device 18 for measuring the ABP, or alternatively, both.

Vital Monitor Device

Figure 9:
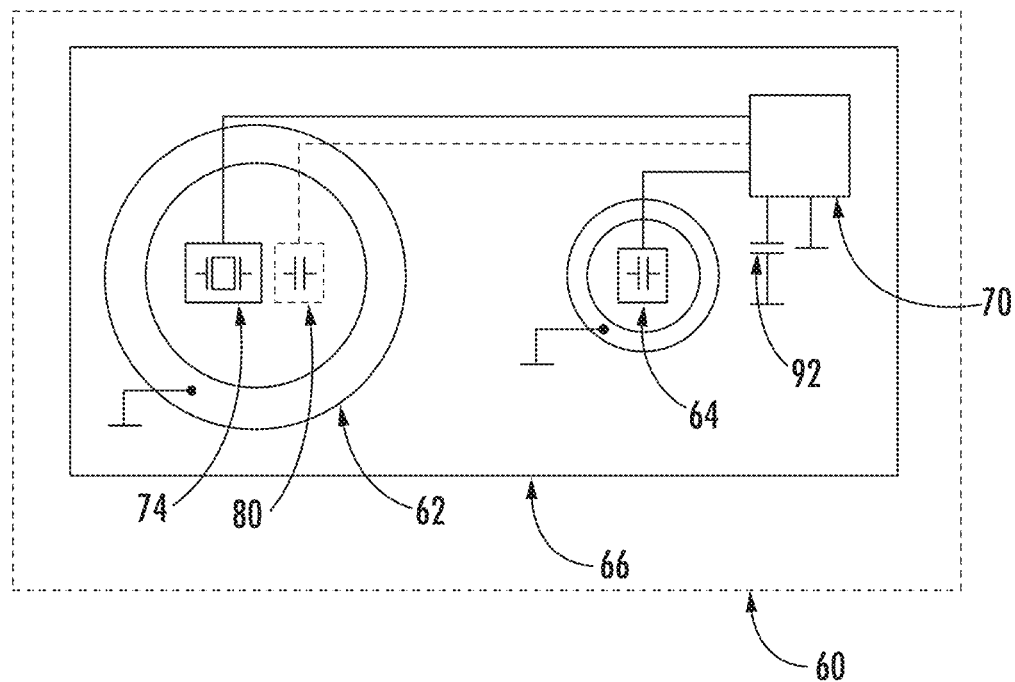
FIGS. 9-11 show an exemplary device for monitoring a patient's vital signs for use with the non-invasive measurement device.
Figure 10:
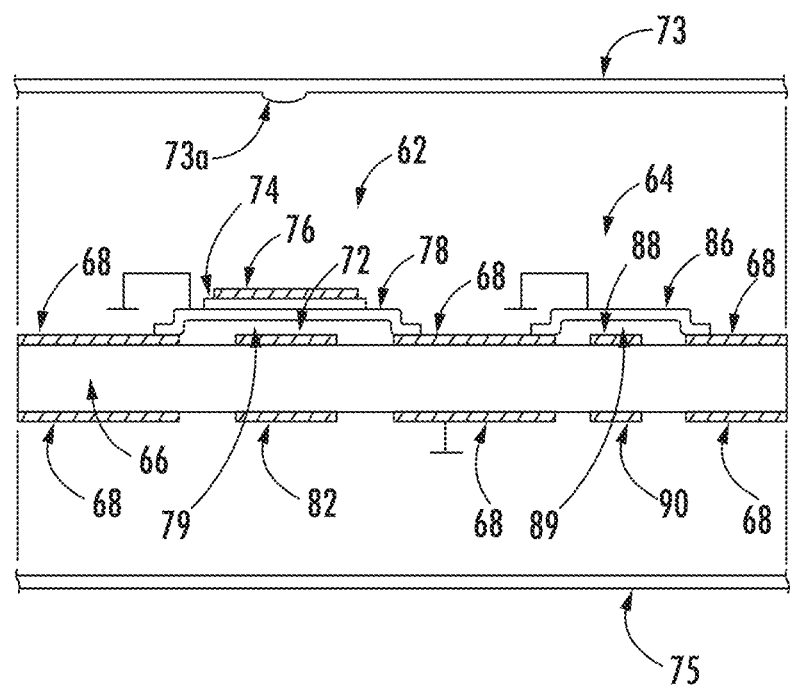
Figure 11:
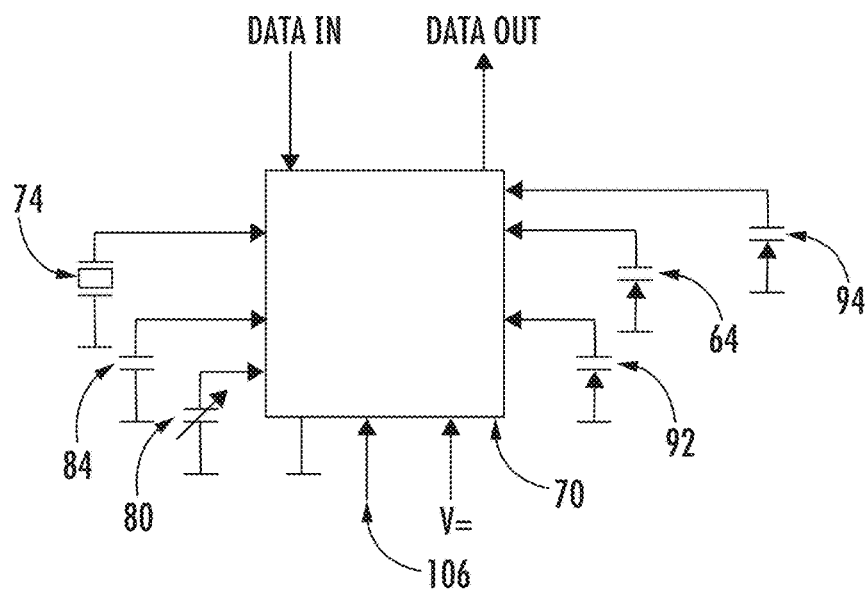

An exemplary device 60 for monitoring patient's vital functions for use with the device 10 for non-invasive monitoring of intracranial pressure (ICP) is shown in FIGS. 9-11. The device 60 may be comprised of a piezoelectric transducer 62, a comparator capacitor 64, a printed circuit board 66, a plating 68 and a computing unit 70, which can be the same or similar to the processor unit 14 described above. The plating 68 may be, for example, copper. The computing unit 70, according to the preferred embodiment, may comprise a single processor, but may also comprise other computing parts communicating with each other by wire or wirelessly.

The piezoelectric transducer 62 utilized here for the purpose of measuring vital functions may be a component for generating sound, such as an electro-acoustic transducer, like a siren or a buzzer, such as, for example, used in watches. The piezoelectric transducer 62 may have suitable mechanical-deformative properties for measuring vital functions. Springs and additional members transferring their deformations caused by movements associated with a patient's vital functions to the measuring element are not necessary, unlike with prior art devices. As a consequence, the device 60 results in lower production costs, higher measuring accuracy, and simplicity. A computing unit 70, such as, for example, a microprocessor unit, which may be used for evaluating contact with a capacitive touchscreen display (e.g., by use of a charge transfer technology or other method), may be utilized in measuring capacity, with a measuring electrode 72 for measuring a static load.

In the exemplary embodiment, the device 60 is on the side of the piezoelectric transducer 62 covered by, for example, a plastic cover 73, which protects the device 60 against water and dust, and at the same time, also removes the mechanical resonance oscillation of the device 60. The cover 73 preferably comprises a protrusion 73*a* that is preferably centered over the piezoelectric transducer 62 so that the protrusion 73*a* contacts the center of the piezoelectric transducer 62 when a force is applied to the cover 73. The device 60 is, on the side, opposite of the piezoelectric transducer 62, covered by, for example, plastic foil 75, which minimizes the height of the entire device 60. The plastic foil may be replaced by any suitable flexible or movable cover, which ensures the transfer of forces to the piezoelectric transducer 62 without its stiffness significantly affecting the resulting force being transmitted to the piezoelectric transducer 62. The device 60 for monitoring a patient's vital functions may be adapted for insertion into a mat, such as the mat 12 described above. The mat can be stored, for example, between the mattress and the bed frame of a bed, in the mattress, or between the mattress and the patient's body, or beneath a pillow, or directly beneath the patient's head. The device 60 may also be adapted for direct placement on the bed frame, and may be detachably fastened, for example, with a snap fastener.

The piezoelectric transducer 62 may be comprised of a piezoelectric element 74, such as from piezoceramics, a first electrode 76 and a second electrode 78. Piezoceramics are, for example, piezoceramic materials based on lead zirconate titanate [Pb[Zr$_x$Ti$_{1-x}$]O$_3$ with 0≤x≤1] or sodium bismuth titanate [NaBi(TiO$_3$)$_2$] or other piezoceramic materials. By using such materials, desired electromechanical properties are achieved, namely, the generation of charge in a suitable range. The piezoelectric element 74 is located between the first electrode 76 and the second electrode 78. The first electrode 76 may be formed, for example, from silver, or optionally from alloys with similar electrical properties. The piezoelectric transducer 62 may have different shapes, such as a circle, a triangle, square, or other shapes. A preferred shape is a circular shape, which ensures the most uniform decomposition of forces. The shape of the piezoelectric transducer 62 may be circular. The piezoelectric transducer 62 may be delimited in its height dimension by, for example, two parallel planes. Preferably, a modification in the form of the piezoelectric transducer 62 can be produced, wherein the center of the piezoelectric transducer 62 is pressed in a direction of an axis perpendicular to one of the delimiting planes so that a board-like shape emerges (i.e., a deflection occurs), where the center of the piezoelectric transducer 62 is located in one plane and the borders of the piezoelectric transducer 62 lie in a plane that lies beneath the center of the piezoelectric transducer 62 so that the second electrode 78 of the piezoelectric transducer 62 does not touch the measuring electrode 72. The board-like shape is best illustrated by the shape of the second electrode 78 (or the entire piezoelectric transducer 62) shown in FIG. 10. As is clearly shown, the board-like shape provides a space distance between the piezoelectric transducer 62 and the measuring electrode 72, resulting in an air gap 79 between the piezoelectric transducer 62 and the measuring electrode 72. The second electrode 78 may be made of brass, aluminum, copper or another metallic material. The locations of the electrodes 76, 78 may be interchangeable, and the piezoelectric element 74 may be positioned in the middle between the electrodes 76, 78. The second electrode 78 may have a circular, or optionally, a board-like shape. Alternatively, the second electrode 78 may have the shape of an ellipse, polygon, or most preferably, a rectangle, square, or other suitable shape. The shape of the second electrode 78 is preferably determined by the shape of the piezoelectric element 74. The second electrode 78 may be flat and its surface, in a rest position, may be approximately parallel to the piezoelectric element 74. The second electrode 78 may be located on the plating 68 for electrical connection with ground. This creates a firm connection with the printed circuit board 66. The second electrode 78 is connected in at least two places to cause the required deformation of the piezoelectric transducer 62. These two connection places may be located, for example, opposite of each other on opposite sides of the length of the piezoelectric transducer 62. In an alternative embodiment, the connection can be provided so that the first electrode 76 is located on the plating 68 and therefore, the piezoelectric transducer 62 is connected with the printed circuit board 66. In a preferred embodiment, the second electrode 78 is connected in at least three places adjoining the printed circuit board 66 to provide greater stability and better deformation of the piezoelectric transducer 62. Preferably, these places where the connections are formed are in the piezoelectric transducer 62 with a circular shape positioned so that the places where the connections are formed create a triangle when connected (i.e., a three-point connection). Alternatively, the piezoelectric transducer 62 may be connected to any fixed board in this way, but by connecting the piezoelectric transducer 62 to the printed circuit board 66, the dimensions of the entire device 60 may be minimized. A measuring capacitor 80, which measures slow actions (i.e., in capacitance) when the device 60 is loaded, may be comprised of the second electrode 78 and the measuring electrode 72. The measuring electrode 72 may be connected to the printed circuit board 66 so as to form an electrode with higher electrical potential. The dielectric of the measuring capacitor 80 may be formed by the air gap 79 between the second electrode 78 of the piezoelectric transducer 62 and the measuring electrode 72. Applying force or load (i.e., pressing) against the piezoelectric transducer 62 varies the distance between the second electrodes 78 of the piezoelectric transducer 62 and the measuring electrode 72. The change in the distance between the second electrode 78 of the piezoelectric transducer 62 and the measuring electrode 72 is proportional to a change in measured capacitance between the second electrode 78 of the piezoelectric transducer 62 and the measuring electrode 72, wherein the capacitance is measured by the computing unit 70. On the opposite side of the printed circuit board 66, opposite the measuring electrode 72, there is a shielding electrode 82 of the measuring capacitor 80. The shielding electrode 82 of the measuring capacitor 80 has the same electrical potential as the measuring electrode 72, and together they can form a shielding measuring capacitor 84, which provides resistance to external influences, for example, by the approximation of metal material. In some cases, two or more piezoelectric transducers 62 may be located on one printed circuit board 66.

The comparator capacitor 64, which is not mechanically loaded, measures change of permittivity of air. The comparator capacitor 64 may comprise a first comparator electrode 86, which can be made, for example, of brass, aluminum, copper or the like. The first comparator electrode 86 may be located on the plating 68 for an electrical connection with ground. The comparator capacitor 64 further may comprise a second comparator electrode 88. The second comparator electrode 88 may be located on the printed circuit board 66 so as to form an electrode with higher electrical potential. The dielectric of the comparator capacitor 64 may be formed by an air gap 89. It should be appreciated that, similar to the measuring capacitor 80 mentioned above, the comparator capacitor 64 may comprise a piezoelectric transducer, comprised of two electrodes separated by a piezoelectric element, wherein one of the two electrodes 86, together with the second comparator electrode 88, forms the comparator capacitor 64. On the opposite side of the printed circuit board 66, opposite of the second comparator electrode 88, is located a shielding electrode 90 of the comparator capacitor 64. The shielding electrode 90 of the comparator capacitor 64 has the same electrical potential as the second comparator electrode 88 and together they can form a shielding comparator capacitor 94, which provides resistance to external influences, for example, by the approximation of metal material. To be clear, there are two shielding electrodes 82, 90, a shielding measuring electrode 82 that shields the measuring capacitor 80 and a shielding comparator electrode 90 that shields the comparator capacitor 64.

The computing unit 70 combines piezoelectric voltage measurement and capacity measurement functions, for example, by means of charge transfer technology. The piezoelectric element 74 is connected to the computing unit 70 through a charge amplifier. Furthermore, the measuring capacitor 80, the comparator capacitor 64, the shielding comparator capacitor 84 and a sampling capacitor 92 are connected to the computing unit 70. The use of the measuring capacitor 80 and the comparator capacitor 64 mitigates changes in the measuring conditions, such as temperature or humidity.

The device 60 may be used for determining intracranial pressure (ICP) according to the above-mentioned methods, or any other suitable method, or for measuring other vital functions. Heartbeat, breath and other vital functions of the patient, such as peristalsis, may generate forces that may be transmitted to the device 60 for monitoring of the same. With respect to the construction of the device 60, the vital functions of the patient are measurable without the need for a permanent or physical connection of the device 60 with the patient's body, for example, by using glue, or via implantation. The device 60 is capable of measuring a patent's vital functions when in contact with the skin of the patient, or when in contact with the patient's clothing, or when transmitted through a mattress on which the patient is placed, or via a mat in which the device 60 for monitoring vital functions may be located or supported. The measuring capacitor 80 and the comparator capacitor 64 may be used to measure slowly changing forces generated by, for example, breathing. During breathing, due to the applied forces, deflection of the central portion of the second electrode 78 (and therefore, to the entire piezoelectric transducer 62) occurs, and thus, a change in the air gap 79 between the second electrode 78 and the measuring electrode 72. Due to the construction of the device 60, where the piezoelectric transducer 62 is attached to the board by one of the electrodes 78, a non-mediated deflection of the piezoelectric transducer 62 is enabled, without the need for additional force transmitting components. The size of the air gap 89 between the first comparator electrode 86 and the second comparator electrode 88 is independent of the action of the forces. The change in the capacity of the measuring capacitor 80 is dependent both on the varying size of the air gap 79 and on the change in permittivity of the air gap 79. The change in the capacity of the comparator capacitor 64 is dependent only on change in permittivity of the air gap 89. The ratio of the capacity of the measuring capacitor 80 and the capacity of the comparator capacitor 64 will remove the dependence of the capacitance change based on the dielectric permittivity and thereby, the independence of changing the measuring conditions. That is to say, the impact of the variable of the permittivity of the air dielectric is effectively removed. The capacity of the comparative capacitor 64 changes with the change of air permittivity—and the same holds true for air permittivity changes in the measuring capacitor 80. This change in the measuring capacitor 80 is compensated for or eliminated by using, considering or factoring in the change of permittivity in the comparative capacitor 64.

Capacity changes are preferably evaluated, for example, by charge transfer technology. The charge transfer technology operates on the principle of charging a capacitor and subsequent transfer of the accumulated charge into the sampling capacitor 92, wherein the number of accumulated charge transfers into the sampling capacitor 92 is counted, until the voltage at the sampling capacitor 92 reaches the same value as a stable reference voltage. It is clear to a person skilled in the art that other methods of measuring capacity can be utilized, for example, a resonance method. In order to measure fast-changing forces caused, for example, by a pulse, a direct piezoelectric effect of piezoelectric material is used, where by deformation of the piezoelectric material due to external forces, a charge which is through a charge amplifier transferred to the computing unit 70 is generated where the voltage is evaluated. Output data is then transmitted via a data wire 96 to a control unit 98. The computing unit 70 can be provided as a microprocessor, with its location on the printed circuit board 66 to ensure protection of the signal because the distance of a transmitted non-digital signal is very short.

Figure 12:
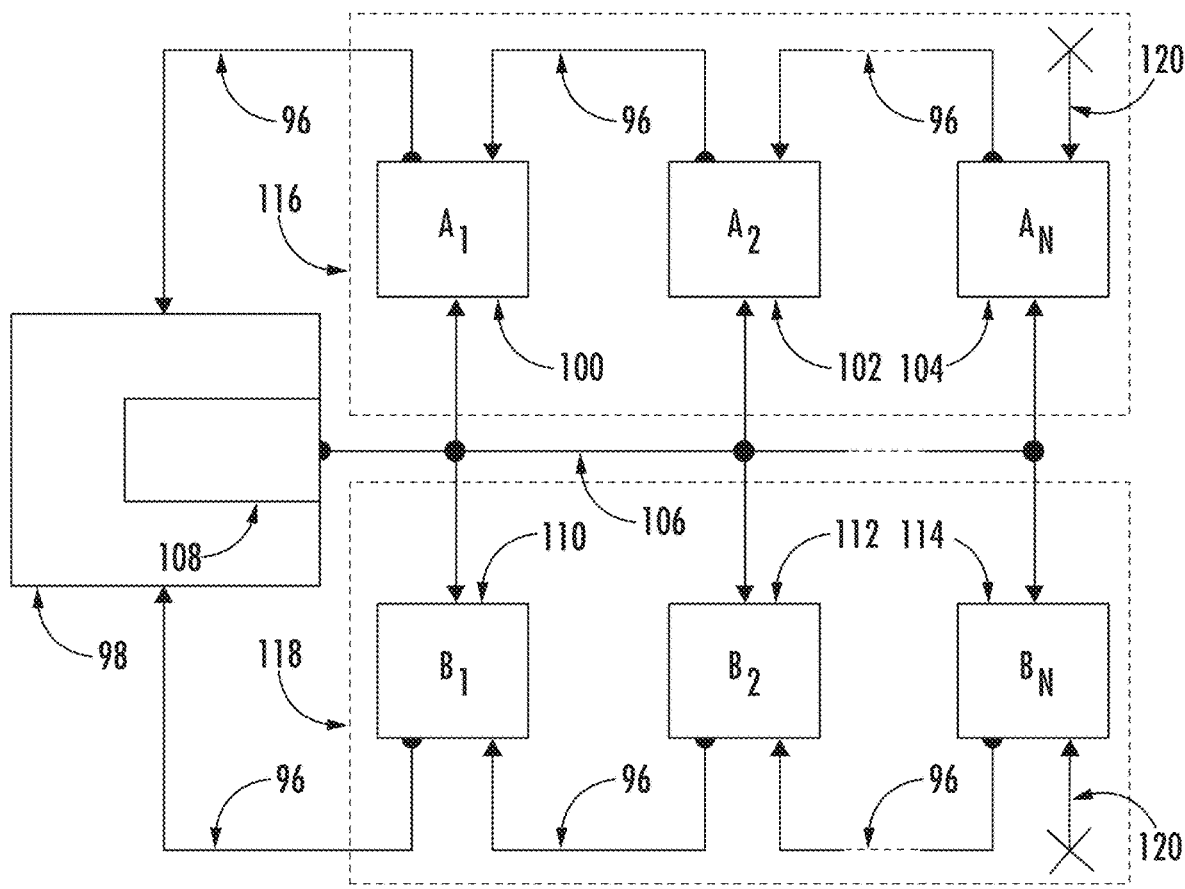
FIG. 12 shows an arrangement of devices for monitoring vital functions of patients.

Further, a method is described for communication of measuring devices $A_a$ to $A_N$ 100, 102, 104, which may be devices 60 for monitoring vital functions of a patient, or sensors of another type, with reference to FIG. 12. A mat, such as the mat 12 described above, may contain a plurality of measuring devices $A_1$ to $A_N$ 100, 102, 104, connected by at least one trigger wire 106 with the control unit 98. The measuring devices $A_1$ to $A_N$ 100, 102, 104 may be connected by the data wire 96 with an adjacent device. The measuring device $A_1$ 100 may also be connected by the data wire 96 with the control unit 98. By connecting the measuring devices $A_1$ to $A_N$ 100, 102, 104 by the data wires 96, a serial data connection of these measuring devices $A_1$ to $A_N$ 100, 102, 104 is established, resulting in a reduction in the required amount of cableway. The trigger wire 106 may be connected to the trigger 108, the task of which is to transmit the signal for initiation of the measurement. Upon receipt of a signal from the trigger 108, a data message from each measuring device $A_K$ (K=<1,N>) is sent through the data wire 96 to the measuring device $A_{K-1}$, which subsequently, sends the data message through the data wire 96 to the measuring device $A_{K-2}$. This way the data message is sent through the data wires 96 to the measuring device $A_1$ 100 from where it is sent through the data wire 96 to the control unit 98. The transfer process is repeated until the data message from the $A_N$ 104 is received in the control unit 98. It should be understood that K takes values from interval 1 to N. Data messages are sent from all measuring devices $A_1$ to AN 100, 102, 104 simultaneously, so that the data message from the measuring device $A_1$ 100 arrives first, then the data message from the measuring device $A_2$ 102 arrives, and finally the data message from the measuring device $A_N$ 104 arrives. The method described above describes only one branch of the measuring device $A_1$ 100 and the measuring device $A_2$ 102 to the measuring device $A_N$ 104. It should be understood that there can be more of these branches connected to the control unit 98 as shown, for example, in FIG. 12, which shows a second branch B, with a measuring device $B_1$ 110, and a measuring device $B_2$ 112, and a measuring device $B_N$ 114.

Data Collection

FIG. 12 is also a schematic view of a medical data collection system. The medical data collection system comprises the control unit 98, a first chain 116 and a second chain 118. The control unit 98 further comprises the trigger 108. The trigger 108 is a unit or feature responsible for providing a time-synchronizing pulse. The trigger 108 can be provided as a single circuit or be a software part of the control unit 98. The time-synchronizing pulse is transmitted via a trigger signal path (trigger wire) 106, with the trigger 108 being connected to each measuring device $A_k$, $B_k$ in the first chain 116 and in the second chain 118. This arrangement permits the synchronization of all measuring devices $A_K$, $B_K$ to one given time. The number of measuring devices is not limited in any way. The measuring devices may be in the following description specified by indices of a series (1, 2, . . . , N–1, N), where N is the number of measuring devices connected in the series, wherein the indices are assigned to the measuring devices in the direction of connection from the closest to the most distant from the control unit 98. The index k is used for a current arbitrary measuring device belonging to the set of measuring devices <1,N>.

Measuring devices $A_K$, $B_K$ are independent from each other. However, all measuring devices $A_K$ in the first chain 116 are connected to a series circuit (or more accurately, as a daisy chain network or scheme). The measuring device $A_N$ 104 is connected to the measuring device $A_{N-1}$ via the data signal path (or data wire) 96 and the measuring device $A_{N-1}$ is connected to the $A_{N-2}$ via the data signal path 96. Such a connection continues through each measuring device $A_k$. The measuring device $A_1$ 100 is connected to the measuring device $A_2$ 102 via the data signal path 96 and the measuring device $A_1$ 100 is connected to the control unit 98 via the data signal path 96. Thus, the control unit 98 and the plurality of measuring devices $A_k$ form a serial connection. Such arrangement requires securing appropriate ends. A terminal wire 120 is thus the representation of blanking of the measuring device $A_N$ 104. The measuring device $A_N$ 104 measures and transmits the data but receives none.

Every measuring device $A_k$, $B_k$ provides a data package. The idea of the medical data collection system is to collect each data package from each measuring device $A_k$, $B_k$ in the control unit 98. When the trigger 108 transmits a time-synchronizing pulse through the trigger signal path 106 to each measuring device $A_k$, the data collection procedure is initiated and the control unit 98 is ready to collect the data packages from the measuring device $A_1$ 100. At the moment each measuring device $A_K$ receives a time-synchronizing pulse, each measuring device $A_k$ starts to both receive and transmit the data packages. Since the measuring device $A_N$ 104 is at the beginning of the measuring device series, it does not receive any data package. The measuring device $A_{K-1}$ is receiving the data package from the measuring device $A_K$ and this procedure continues until the data package from measuring device $A_N$ 104 is received by the control unit 98. Each measuring device $A_k$ performs the same procedure. Thus, this cascading procedure leads to the collection of all data packages in the control unit 98.

The measuring devices $B_k$ in the second chain 118 form the same serial connection as described above. The data collection procedure is also initiated by the time-synchronizing impulse from the trigger 108 and the cascade procedure of data package collection is performed from the measuring device $B_2$ 112 via all measuring devices $B_k$ to the measuring device $B_2$ 112 and the measuring device $B_1$ 110, which finally transmits data packages to the control unit 98.

In the preferred embodiment, data packages are the same size. Data packages of the same size ensure optimal time of data package transmission and receiving. However, this does not limit the present invention, since it is obvious to the person skilled in the art that the transmitting and receiving time could be optimized by utilizing additional software in each measuring device. In addition, the illustrated embodiment is only illustrative. The invention is not intended to be limited to the embodiment shown. A person skilled in the art could implement the present invention in the range of applications and thus, use other embodiments, such as a connection of bed sensors, sensors of vital functions, bed exit sensors, brake sensors, bed tilt sensors or any other sensor relating to medical data or condition collection.

In addition, it is clear to a person skilled in the art that the data collection system is not limited by two chains. It should be noted that the number of chains is not intended to be limited. Furthermore, it should be clear that, in some applications, the connection via both the trigger signal path 106 and the data signal path 96 could be wireless.

In yet another embodiment, data packages could be divided into smaller packages. In such case, the receiving and transmitting of one or more parts of a data package could be performed simultaneously. The measuring device $A_k$ can receive part of a data package from the measuring device $A_{k+1}$ and at the same time, transmit the part of the data package received to the measuring device $A_{k-1}$ before the whole data package of the measuring device $A_{k+1}$ is stored in the measuring device $A_k$.

Using the system described above provides other positive effects, for example, data transmitted from each measuring device does not need additional overhead data. The overhead data can be, for example, packet header, packet footer, packet checksum, server bits, and so on. The data package can in some embodiments may comprise a checksum, parity bits or cyclic redundancy checks to detect errors that occur during transmission.

This method may be used on measuring devices for measuring patient's vital functions, such as are heartbeat, respiration, apnea, peristalsis or twitches of the patient's head related to the intracranial pressure. This data can be considered data associated with patient's vital functions.

The data collection system and method can be used with the highest efficiency on multi-sensor measuring devices, like the device 60 described in detail above.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

LIST OF REFERENCE NUMBERS 10 device for non-invasive ICP measurement
12 measuring mat
14 processor unit
16 device for measurement of electrical activity of the heart
18 device for invasive measurement of arterial pressure
20 displaying unit
22 network connector
24 sensor (in the mat)
28 mattress
30 hospital bed
40 cranial cavity
42 bloodstream hemodynamics
44 heart
46 area I
48 area II
50 area III
60 device for monitoring patient's vital functions
62 transducer
64 comparator capacitor
66 printed circuit board
68 plating
70 computing unit
72 measuring electrode
73 cover
73a protrusion
74 piezoelectric element
75 plastic foil
76 first electrode
78 second electrode
79 air gap
80 measuring capacitor
82 shielding electrode of measuring capacitor
84 shielding measuring capacitor 86 first comparator electrode
88 second comparator electrode
89 air gap
90 shielding electrode of comparator capacitor
92 sampling capacitor
94 shielding comparator capacitor
96 data wire
98 control unit
100 measuring element $A_1$
102 measuring element $A_2$
104 measuring element $A_N$
106 trigger wire
108 trigger
110 measuring device $B_1$
112 measuring device $B_2$
114 measuring device $B_N$
116 first chain
118 second chain
120 terminal wire

What is claimed is:

1. A device for non-invasive monitoring of intracranial pressure (ICP) of the patient, the device comprising:
a measuring mat comprising a substantially flat piece of material configured for placement under the head of the patient for continuously monitoring the ICP of the patient, the measuring mat comprising at least one sensor comprising a piezoelectric sensor with third conductive capacity electrode for measuring of mechanical manifestations of the head of the patient, the mechanical manifestations being in the form of micro movements and mechanical vibrations caused by the patient's bloodstream hemodynamics,
a reference device having an output signal comprising mechanical manifestations of the bloodstream of the patient, and
a processor unit for determining the time delay between a first signal from the reference device corresponding to the output signal comprising the mechanical manifestations of the bloodstream of the patient and a second signal from the at least one sensor of the measuring mat corresponding to the mechanical manifestations of the head of the patient, wherein the time delay is related to a reflection of a pulse wave of the bloodstream of the patient's head, and for converting the time delay into the ICP of the patient, wherein the output signal comprises electrocardiogram (ECG) or blood pressure signal and the first signal comprises an R wave in an ECG signal.

2. The device for non-invasive monitoring of ICP of the patient in accordance with claim 1, wherein the at least one sensor for measurement of mechanical manifestations of the head comprises a piezoelectric element.

3. The device for non-invasive monitoring of ICP of the patient in accordance with claim 1, wherein the at least one sensor for measurement of mechanical manifestations of the head comprises a tensometer.

4. The device for non-invasive monitoring of ICP of the patient in accordance with claim 1, wherein the at least one sensor for measurement of mechanical manifestations of the head comprises an accelerometer.

5. The device for non-invasive monitoring of ICP of the patient in accordance with claim 1, wherein the at least one sensor for measurement of mechanical manifestations of the head comprises a capacity sensor.

6. The device for non-invasive monitoring of ICP of the patient in accordance with claim 1, wherein the processor unit is connected with the measuring mat for processing the first and second signal.

7. The device for non-invasive monitoring of ICP of the patient in accordance with claim 1, wherein the processor unit is located inside the measuring mat.

8. The device for non-invasive monitoring of ICP of the patient in accordance with claim 1, wherein the ICP of the patient is measured pressure inside the head of the patient.

9. The device for non-invasive monitoring of ICP of the patient in accordance with claim 1, wherein the reference device is at least one device selected from a group of devices comprising an electrocardiogram, a vectorcardiogram and a ballistocardiogram.

10. The device for non-invasive monitoring of ICP of the patient in accordance with claim 1, wherein the reference device is a device for measurement of arterial blood pressure.

11. The device for non-invasive monitoring of ICP of the patient in accordance with claim 1, wherein the ICP is a calculated absolute value.

12. The device for non-invasive monitoring of ICP of the patient in accordance with claim 1, wherein the processor unit is connected to a displaying device.

13. The device for non-invasive monitoring of ICP of the patient in accordance with claim 12 is wherein the displaying device is part of the device for non-invasive monitoring of ICP of the patient.

14. The device for non-invasive monitoring of ICP of the patient in accordance with claim 12, wherein the displaying device is part of a patient monitor.

15. The device for non-invasive monitoring of ICP of the patient in accordance with claim 12, wherein the displaying device is separate from the device for non-invasive monitoring of ICP of the patient.

16. The device for non-invasive monitoring of ICP of the patient in accordance with claim 12, wherein the displaying device or the processor unit is connected via a network connector to the hospital system for collection of patient data.

17. The device for non-invasive monitoring of ICP of the patient in accordance with claim 12, wherein the displaying device or the processor unit is connected via wireless technology to the hospital system for collection of patient data.

18. A method for device for non-invasive measurement of ICP of the patient of claim 1, comprising the steps of:
a) communicating, via the processor unit, with the measuring mat and the reference device,
b) sending, via the reference device and the at least sensor of the measuring mat respectively, the first and second signals to the processor unit,
c) recording and storing, via the processor unit, the times of receiving the first signal from the reference device corresponding to the output signal comprising the mechanical manifestations of the bloodstream of the patient and the time of receiving the second signal from the at least sensor of the measuring mat corresponding to the mechanical manifestation of the head of the patient,
d) calculating, via the processor unit, the time delay between the first and second signal, wherein the time delay relates to the reflection of the pulse wave of the bloodstream of the patient's head and
e) converting, via the processor unit, the delay to the ICP of the patient, wherein the output signal comprises the ECG or the blood pressure signal and the first signal comprises the R wave in the ECG signal.

19. The method for device for non-invasive measurement of ICP of the patient in accordance with claim 18, wherein the ICP is measured pressure inside the head of the patient.

20. A device for non-invasive monitoring of intracranial pressure (ICP) of the patient, the device comprising:
a measuring mat comprising a substantially flat piece of material configured for placement under the head of the patient for continuously monitoring the ICP of the patient, the measuring mat comprising at least one sensor for measurement of mechanical manifestations of the head, the mechanical manifestations being in the form of micro movements and mechanical vibrations caused by the patient's bloodstream hemodynamics,
at least one reference device for measurement of mechanical manifestations comprising at least one of heart activity or arterial blood pressure (ABP) of the patient,
a processor unit for determining a time delay T between a first signal related to at least one of information either in a heart cycle of the patient or blood pressure of the patient from the reference device and a second signal related to a time when a pulse wave is reflected in the bloodstream in the head of the patient originating from the at least one sensor of the measuring mat, and for converting the time delay T into the ICP of the patient,
wherein the following equations are used for converting the time delay T into the ICP of the patient:

$$CPP = -A \cdot \log(T - T_0), \text{ and}$$

$$ABP - CPP = ICP$$

where CPP is a cerebral perfusion pressure, A is an empirically determined constant, $T_0$ is the time corresponding to the reflection time at infinite ICP.

21. The device for non-invasive monitoring of ICP of the patient in accordance with claim 20, wherein the at least one sensor for measurement of mechanical manifestations of the head comprises a piezoelectric element.

22. The device for non-invasive monitoring of ICP of the patient in accordance with claim 20, wherein the at least one sensor for measurement of mechanical manifestations of the head comprises a tensometer.

23. The device for non-invasive monitoring of ICP of the patient in accordance with claim 20, wherein the at least one sensor for measurement of mechanical manifestations of the head comprises an accelerometer.

24. The device for non-invasive monitoring of ICP of the patient in accordance with claim 20, wherein the at least one sensor for measurement of mechanical manifestations of the head comprises a capacity sensor.

25. The device for non-invasive monitoring of ICP of the patient in accordance with claim 20, wherein the processor unit is connected with the reference device for processing the first signal.

26. The device for non-invasive monitoring of ICP of the patient in accordance with claim 20, wherein the processor unit is connected with the measuring mat for processing the second signal.

27. The device for non-invasive monitoring of ICP of the patient in accordance with claim 20, wherein the processor unit is located inside the measuring mat.

28. The device for non-invasive monitoring of ICP of the patient in accordance with claim 20, wherein the reference device is at least one device selected from a group of devices comprising an electrocardiogram, a vectorcardiogram and a ballistocardiogram.

29. The device for non-invasive monitoring of ICP of the patient in accordance with claim 20, further comprising a device having an output signal comprising information about blood pressure of the patient.

30. The device for non-invasive monitoring of ICP of the patient in accordance with claim 20, wherein the processor unit is connected to a displaying device.

31. The device for non-invasive monitoring of ICP of the patient in accordance with claim 30, wherein the displaying device is part of the device for non-invasive monitoring of ICP of the patient.

32. The device for non-invasive monitoring of ICP of the patient in accordance with claim 30, wherein the displaying device is part of a patient monitor.

33. The device for non-invasive monitoring of ICP of the patient in accordance with claim 30, wherein the displaying device is separate from the device for non-invasive monitoring of ICP of the patient.

34. The device for non-invasive monitoring of ICP of the patient in accordance with claim 30, wherein the displaying device or the processor unit is connected via a network connector to a hospital system for collection of patient data.

35. The device for non-invasive monitoring of ICP of the patient in accordance with claim 30, wherein the displaying device or the processor unit is connected via wireless technology to a hospital system for collection of patient data.

* * * * *